(12) United States Patent
Peterson

(10) Patent No.: US 8,889,631 B2
(45) Date of Patent: *Nov. 18, 2014

(54) DISRUPTORS OF EARLY/RECYCLING ENDOSOMES

(75) Inventor: Blake R. Peterson, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 894 days.

This patent is subject to a terminal disclaimer.

(21) Appl. No.: 12/543,313

(22) Filed: Aug. 18, 2009

(65) Prior Publication Data

US 2010/0041773 A1    Feb. 18, 2010

Related U.S. Application Data

(60) Provisional application No. 61/089,710, filed on Aug. 18, 2008.

(51) Int. Cl.
| | |
|---|---|
| A61K 38/00 | (2006.01) |
| A61K 47/42 | (2006.01) |
| C07K 7/08 | (2006.01) |
| C07K 9/00 | (2006.01) |
| A61K 47/48 | (2006.01) |

(52) U.S. Cl.
CPC ..... *A61K 47/48338* (2013.01); *A61K 47/48123* (2013.01)
USPC ........... 514/20.9; 514/1.2; 514/773; 530/322; 530/326

(58) Field of Classification Search
CPC .................. A61K 47/48338; A61K 47/48123
USPC ................................. 514/773; 530/322, 326
See application file for complete search history.

(56) References Cited

U.S. PATENT DOCUMENTS

2004/0146867 A1\* 7/2004 Slattum et al. ..................... 435/6
2006/0229235 A1\* 10/2006 Peterson ......................... 514/7

OTHER PUBLICATIONS

Sun et al. Jul. 10, 2008, JACS, vol. 130, pp. 10064-10065.\*
Boonyarattanakalin et al. 2004, J. Am. Chem. Soc. 2004, 126, 16379-16386.\*
Sun Q., et al., Selective Disruption of Early/Recycling Endosomes: Release of Disulfide-Linked Cargo Mediated by a N-Alkyl-3beta-Cholesterylamine-Cappped Peptide, Journal of American Chemical Society, Jul. 10, 2008, vol. 130 pp. 10064-10065, Web Publication.
Peterson B.R. et al., Synthetic Mimics of Mammalian Cell Surface Receptors: Prosthetic Molecules that Augment Living Cells, Organic and Biomolecular Chemistry, 2005, vol. 3, No. 20, pp. 3607-3612.
Hirosue S. et al., pH-Dependent Lytic Peptide Discovered by Phage Display, Biochemistry, 2006 vol. 45, pp. 6476-6487.
Wolff J.A. et al., Breakin gthe Bonds: Non-Viral Vectors Become Chemically Dynamic, Molecular Therapy, Jan. 2008, vol. 16, No. 1, pp. 8-15.

\* cited by examiner

*Primary Examiner* — Janet Epps-Smith
(74) *Attorney, Agent, or Firm* — Maschoff Brennan, PLLC

(57) ABSTRACT

A delivery system for introducing a cargo molecule into cytosol of a living cell can include: a first membrane binding element linked to an endosomal compartment disrupting element through a first linker having one or more anionic moieties; and a second membrane binding element linked to an exogenous cargo molecule through a second linker having one or more anionic moieties, the second linker having a region that is selectively cleavable, wherein the first and second membrane binding elements both induce endocytosis into an early/recycling endosome and the endosomal compartment disrupting element destabilizes the early/recycling endosome such that the exogenous cargo molecule is released from the second membrane binding element and into the cytosol of the living cell.

33 Claims, 15 Drawing Sheets

3 + 2

3 + 2 + chloroquine 3 alone

DISRUPTORS OF EARLY/RECYCLING ENDOSOMES

CROSS-REFERENCE TO RELATED APPLICATIONS

This patent application claims benefit of U.S. patent application having Ser. No. 61/089,710, filed on Aug. 18, 2008, which provisional application is incorporated in its entirety by specific reference.

STATEMENT REGARDING FEDERALLY SPONSORED RESEARCH OR DEVELOPMENT

This invention was made with government support under CA-83831 awarded by the National Institutes of Health. The government has certain rights in the invention.

BACKGROUND OF THE INVENTION

It is often difficult to deliver compounds, such as proteins, peptides, nucleic acids and other drugs and diagnostic compounds intracellularly because cell membranes resist the passage of these compounds.

One method for transmembrane delivery of exogenous molecules is based on the mechanism of receptor-mediated endocytosis (RME). RME is a major mechanism of uptake of impermeant molecules by mammalian cells. In this process, extracellular ligands bind cell surface receptors that cluster in dynamic regions of cellular plasma membranes. By actively pinching off to form intracellular vesicles, these membrane regions are internalized, encapsulating ligand-receptor complexes in the cytoplasm.

Receptor-mediated endocytosis (RME) is a major mechanism of uptake of impermeant molecules by mammalian cells (Conner, S. D.; Schmid, S. L. *Nature* 2003, 422, 37-44). In this process, extracellular ligands bind cell surface receptors that cluster in dynamic regions of cellular plasma membranes. By actively pinching off to form intracellular vesicles, these membrane regions are internalized, encapsulating ligand-receptor complexes in the cytoplasm. These vesicles fuse and form early (primary/sorting) endosomes that are acidified (pH~6) by the activation of proton pumps, conditions that generally promote the dissociation of receptors from bound ligands. Free receptors often cycle back to the cell surface, generally via subsequent trafficking through related recycling endosomes (also termed the endocytic recycling compartment) (Maxfield, F. R.; McGraw, T. E. *Nat. Rev. Mol. Cell. Biol.* 2004, 5, 121-132). In contrast, free ligands are typically directed to more acidic late endosomes and lysosomes (pH~5), where hydrolases and other enzymes promote their degradation. Some viruses and other intracellular pathogens exploit RME to enter cells, but these organisms avoid degradation in lysosomes by expressing pH-dependent fusogenic proteins that disrupt endosomal membranes (Lakadamyali, M.; Rust, M. J.; Zhuang, X. *Microbes Infect.* 2004, 6, 929-836). To escape entrapment within these membranes and gain access to the cytosol, Semliki Forest virus disrupts early endosomes whereas influenza virus disrupts late endosomes during the course of infection. Nevertheless, many exogenous molecules that are introduced into cells using RME are not able to escape degradation in the late endosomes or the lysosome.

BRIEF SUMMARY OF THE INVENTION

In one embodiment, the present invention can include a delivery system for introducing a cargo molecule into cytosol of a living cell. The system can include: a first membrane binding element linked to an endosomal compartment disrupting element through a first linker having one or more anionic moieties; and a second membrane binding element linked to an exogenous cargo molecule through a second linker having one or more anionic moieties, the second linker having a region that is selectively cleavable, wherein the first and second membrane binding elements both induce endocytosis into an early/recycle endosome and the endosomal compartment disrupting element destabilizes the early/recycling endosome such that the exogenous cargo molecule is released from the second membrane binding element and into the cytosol of the living cell.

In one embodiment, the present invention can include a delivery platform for introducing a cargo molecule into cytosol of a living cell. The platform can include: a membrane binding element; a branched ionic linker linked to the membrane binding element, the linker having a selectively cleavable region; an endosomal compartment disrupting element linked to a branch of the branched anionic linker; and an exogenous cargo molecule linked to a branch of the branched anionic linker through the selectively cleavable region, wherein the membrane binding element induces endocytosis into an early/recycle endosome and the endosomal compartment disrupting element destabilizes the early/recycling endosome such that the exogenous cargo molecule is released from the early/recycle endosome and into the cytosol of the living cell.

The platform or system can be configured as follows: the membrane binding elements can be cholesterylamine derivatives, such as N-alkyl-cholesterylamine derivatives or dihydrocholesterylamine derivatives; 3beta-amino-5alpha-cholestane or its derivatives; the linkers can be straight or branched, substituted or unsubstituted and between C1-C20 atoms or hetero-atom; the one or more anionic moieties of linkers can be located in the linker proximal to the N-alkyl-cholesterylamine derivatives relative to the endosomal compartment disrupting element or cargo molecule; the anionic moieties can include acidic functional groups, such as acidic amino acid side groups aspartic acid and/or glutamic acid groups; the linker region that is selectively cleavable can include a substrate for a protease, such as a protease that is preferentially present in specific type of cell; the linker region can be selectively cleavable by a substance preferentially located in cytosol compared to extracellular locations or a lysosome, such as the region including a disulfide linker; the endosomal compartment disrupting element can include at least one of a PC4 peptide, a PC4 peptide related sequence, a PC4 D-peptide variant that includes at least one D-amino acid, a peptidomimetic, derivatives thereof, and combinations thereof, which for example, the PC4 peptide can have an amino sequence AcNH(SSAWWSYWPPVA) (SEQ ID NO: 1); and the exogenous cargo molecule is selected from the group consisting of drugs, prodrugs, molecular probes, oligopeptides, polypeptides, proteins, oligonucleotides, polynucleotides, DNA, RNA, siRNA, nucleic acids, carbohydrates, or lipids, and combinations thereof, such as a cancer therapeutic agent being an example.

In one embodiment, the membrane binding elements is an N-alkyl-cholesterylamine derivative, the linker includes two or more anionic moieties that include acidic functional groups, and the endosomal compartment disrupting element is a polypeptide. The acidic functional groups can be from aspartic acid and/or glutamic acid groups. The linker region can be selectively cleavable includes a substrate for a protease or is selectively cleavable by a substance preferentially located in cytosol compared to extracellular locations or a lysosome.

In one embodiment, the present invention can include a method for introducing a cargo molecule into cytosol of a living cell. Such a method can include providing a delivery platform or system as described herein; and administering the delivery platform or system to a subject having the living cell such that the membrane binding elements associate with the living cell so as to induce endocytosis of the delivery system into an early/recycling endosome that acidifies so as to induce the endosomal compartment disrupting element to destabilize the endosome so that cytosol enters into the endosome and the selectively cleavable region is cleaved so as to allow for the release of the cargo molecule from the early/recycling endosome into the cytosol.

Another method can be performed as follows: providing a delivery platform or system as described herein; administering the delivery platform or system to a subject having the living cell such that the membrane binding elements associate with the living cell so as to induce endocytosis of the delivery system into an early/recycling endosome; exposing the selectively cleavable region to a protease or cytosol substance that cleaves the cleavable region; and disrupting the endosome with the endosomal compartment disrupting element to release of the cargo molecule from the early/recycling endosome into the cytosol.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIGS. 4A-4F show CHO cells were treated with Compound 3 or Compound 4 (5 µM) and Compounds 1, 2, or 5 (8 µM) for 24 h. In FIG. 4F, [chloroquine]=5 µM. In FIGS. 4G-4J, Jurkat lymphocytes were treated with Compound 3 or Compound 4 (2.5 µM) and Compound 1 or Compound 5 (2 µM) for 12 h.

In FIG. 9B, bafilomycin A1 (1 µM), a vacuolar $H^+$ ATPase inhibitor that blocks acidification of endosomes, was added. FIG. 9A is without bafilomyin. Cells were washed with media and imaged by DIC and confocal laser scanning microscopy.

FIG. 10A shows CHO cells treated with Compound 3 (5 µM) and Compound 1 or Compound 5 for 24 h at 37° C. and trypsinized for analysis. FIG. 10B shows Jurkat lymphocytes treated with Compound 3 (2.5 µM) and Compound 1 or Compound 5 for 12 h at 37° C. Cellular fluorescence was analyzed by flow cytometry. The acidity of early/recycling endosomes quenches the fluorescence of Compound 3, and treatment with Compound 1 was observed to enhance cellular fluorescence as a consequence of disruption of these acidic compartments.

FIG. 13 compares structures of the PC4-derived endosome disruptor (Compound 1 disclosed as SEQ ID NO: 2) compared with a related MMP-2 substrate (Compound 45 disclosed as SEQ ID NO: 8) designed to disrupt endosomes upon cleavage by including the terminal polar region. PC4 disclosed as SEQ ID NO: 1.

DETAILED DESCRIPTION OF THE ILLUSTRATED EMBODIMENTS

Figure 1:
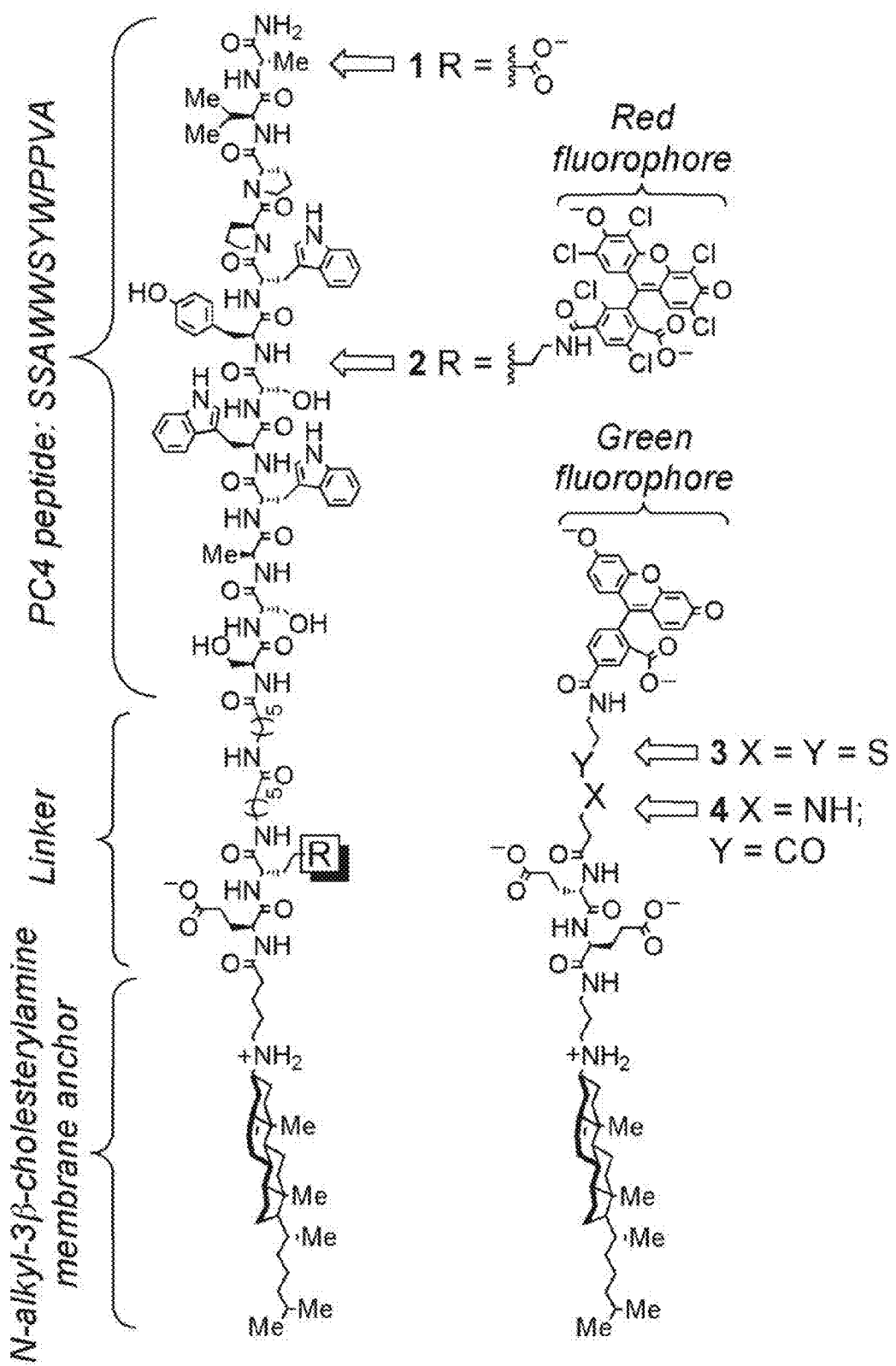
FIG. 1 shows compounds of the present invention with Compound 1. PC4 peptide disclosed as SEQ ID NO: 1. Full length compound disclosed as SEQ ID NO: 7.

The present invention is related to delivery platforms and systems, and methods for using the platforms and systems for delivering an exogenous cargo molecule (i.e., agent) to a target cell via a synthetic ligand that may be capable of employing receptor-mediated endocytosis. The delivery platforms and systems can include: a receptor-targeting or membrane-binding ligand; a selectively cleavable anionic linker, an agent to be delivered into a cell, and an endosomal disruption member. These components can be combined and linked in various embodiments as described herein ranging from a dual component system or a single substance that has all of these components.

The delivery platforms and systems can be used to deliver various agents selected from a protein, peptide, polypeptide, nucleic acid (RNA, DNA, RNA/DNA hybrid, or a mimic thereof such as PNA, morpholinos, and related oligomers), siRNA, carbohydrates, lipids, marker, luminophore, tracer substance, molecular probe, oligopeptide, drug, prodrug, a small molecule, or other like agent as well as combinations thereof into a cell via endocytosis.

As used herein, a delivery platform is considered to be a single substance that has the components of the invention, whereas a system can include multiple substances that together have the components of the invention.

The use of endocytic uptake pathways to deliver poorly permeable molecules into mammalian cells is often plagued by entrapment and degradation of material in late endosomes and lysosomes. As a strategy to prevent the exposure of cargo to these highly hydrolytic membrane-sealed compartments, derivatives of the membrane anchor cholesterylamines (e.g., N-alkyl-3β-cholesterylamine, dihydrocholesterylamine, 3beta-amino-5alpha-cholestane) were prepared that deliver via endocytosis a cargo molecule to less hydrolytic early/recycling endosomes. Additionally, utilizing a selective pH-dependent membrane-lytic dodecapeptide with the membrane anchor (e.g., ligand) allows for the cargo molecule to escape from the early endosomal compartments, which is evidenced by data obtained in Chinese hamster ovary cells or Jurkat lymphocytes. The combination of the ligand that targets early/recycling endosomes as well as a pH-dependent membrane disruption member allows for the cargo to be capable of escaping from the disrupted membranes of early/recycling endosomes. Additionally, utilization of a selectively cleavable linker to link the ligand and cargo can allow for enhanced escape of the cargo from the early/recycling endosome. For example, a disulfide-containing linker or a linker susceptible to proteolytic cleavage can be employed, and can result in cleavage of the linker and escape of the cargo as exemplified with a fluorophore escaping into the cytosol and nucleus with low toxicity. The ability of appropriately designed N-alkyl-3β-cholesterylamines to deliver cargo into and release selectively cleavable-linked cargo from relatively non-hydrolytic early/recycling endosomes can be useful for the delivery of a variety of sensitive molecules into living mammalian cells.

It has been found that delivery systems that include a synthetic membrane anchor of a cholesterylamine derivative (e.g., N-alkyl-3β-cholesterylamine) linked to an agent can induce endocytosis into the early endosomal recycling system. When the system includes an early endosomal disrupting member the early endosomal recycling system as well as having the cholesterylamine ligand being linked to the agent with a selectively cleavable linker with anionic moieties, the agent can escape from the early/recycling endosome. Accordingly, the delivery system can be actively inserted into the outer leaflet of plasma membranes of mammalian cells and the agent can be released before the ligand undergoes rapid endocytotic plasma membrane recycling. This ability of N-alkyl-3β-cholesterylamine derivatives to cycle between the cell surface and early/recycling endosomes allows the delivery system to promote the cellular uptake of cell-impermeable compounds by functionally mimicking receptors involved in receptor-mediated endocytosis. The selectively cleavable linkers and early endosomal disrupting member can allow for release of the agent into the cytosol without being irreversibly delivered into late endosomes/lysosomes. Thus, a delivery system that includes a cholesterylamine derivative targeting moiety linked through a selectively cleavable linker having anionic moieties to an agent and includes an early endosomal disrupting member can deliver the agent into the cytosol of a cell, and thereby avoid the degradation of the agent by the late endosome/lysosome.

The platform and systems of the invention can be used for methods of delivering an exogenous cargo molecule (e.g., agent) to a target cell via a receptor or membrane association that endocytoses a synthetic ligand. Membrane binding elements are considered to be ligands as described herein by generally associating with the cell surface membrane or a receptor or other protein on the cell surface in a manner that induces endocytosis into an early/recycling endosome. The platform system can include a receptor-targeting ligand that is linked to both an endosomal compartment disruptor and an exogenous cargo molecule for introducing the exogenous cargo molecule into a target cell via endocytosis and out of the endosome into the cytosol via endosomal destabilization. The methods disclosed herein can be used to deliver a desired exogenous cargo molecule to a target cell in situations, for example, where the cell is either impermeable to the exogenous molecule or the exogenous molecule would be subject to degradation in the cell if it were engulfed into the cell via native endocytosis pathways.

A system can include a first ligand linked to an endosomal compartment disrupting element and a second ligand linked to an exogenous cargo molecule through a selectively cleavable anionic linker.

In one embodiment, the endosomal compartment disrupting element and the exogenous cargo molecule are linked to the same ligand as opposed to having them linked to separate ligands. The system includes a membrane binding element coupled to a branched linker that is linked to both to an endosomal compartment disrupting element and an exogenous cargo molecule. The linker includes at least one selectively cleavable site and is anionic. As such, the linker can be configured to cleave to release the cargo with or without also releasing the endosomal disrupter.

In one embodiment, the ligands are selected from the group consisting of cholesterol, cholesterylamine, dihydrocholesterylamine, a lipid, a fatty acid, derivatives thereof, and combinations thereof. For example, a suitable ligand can be a membrane-binding element that can be incorporated in the system for the introduction of a molecule into a target cell is a derivative of 3β-cholesterylamine or dihydrocholesterylamine. Examples of specific derivatives of 3β-cholesterylamines include N-alkyls that can be straight chain, branched, substituted or unsubstituted, from C1-C20, C2-C12, C1-C10, or the like. An example of an N-alkyl-3β-cholesterylamine is shown in FIG. 1 as the membrane anchor. It can also be 3β-amino-5alpha-cholestane, which is considered to be a derivative thereof.

It has been found, for example, that the makeup of the linker region affects the partitioning of these compounds between the plasma membrane and endosomal compartments. As such, the linker includes at least one anionic moiety, and more preferably two or more separate or contiguous anionic moieties. The anionic moieties can be any of a variety of components that present an anionic feature at physiological conditions within the blood of extracellular fluids. The anionic moieties on the linker have been found to enhance the ability of the cholesterylamine derivatives to bind or have affinity for the cells. The inclusion of one or more anionic moieties in the linker has surprising and unexpected results in that the cholesterylamines have enhanced ability to function as a ligand and promote endocytosis into early/recycling endosomes. In part, this is surprising due to the fact that the cell membranes are overwhelming negative in charge by being comprised of anionic lipids, and one would expect that anionic linkers would be repulsed by the anionic cell membrane.

The linker anionic moiety can be obtained by including at least one acidic substance, such as an amino acid (e.g., standard or non-standard) having an acidic side chain. Examples of acidic amino acids that can be included in the linker are aspartic acid or glutamic acid. Also, the anionic moiety can include one or more of the following: alkyls having an anionic side group or substituent (e.g., carboxyl groups, phosphate groups and/or sulfate groups), or the like. Also, the anionic moiety can include one or more anionic monomers derived from carrageenans, alginates, agar, pectins, modified pectins, gellan gum, xanthan gum, furcellaran, cellulose derivatives, particularly carboxymethyl cellulose (CMC) and cellulose sulfate, dextran sulfate, modified starches, exopolysaccharides and the like. Of course, other anionic substances that can be prepared to into linkers linking the ligand to the endosomal disrupter or agent can be included that have a first linking end, a second linking end, and an anionic moiety so as to contain at least one anionic functional group or be overall anionic when functioning as a part of a linker.

The cleavable motifs of the linkers that can be cleaved under physiological conditions can include one or more of a disulfide, a cleavable peptide, a ribonucleic acid, an ester, or another group or molecule that can be cleaved in early/recycling endosomes or when exposed to cellular cytoplasm. Examples of substances that can cleave the cleavable linker under physiological conditions and that are typically found in the cytoplasm of a cell include, but are not limited to, cellular glutathione, proteases, esterases, and RNase. In a preferred embodiment the substance that cleaves the cleavable linker (e.g., disulfide) is cellular glutathione. Cleavable peptides can be represented by MMP-2 cleavable motif.

Overall, the linker can vary in length and configuration. The linker can be an alkyl chain that is a straight chain, branched, substituted or unsubstituted, from C1-C20, C2-C12, C1-C10, or the like. A branched linker can be linked to one ligand and to both the endosomal disrupter and the cargo molecule. The linker can include amino acids and/or alkyl groups as described herein. The anionic moieties can be on proximal to the ligand, proximal to the endosomal disrupter or distributed therein. With regard to the cargo-carrying platform, the anionic moieties can be on the ligand side of the cleavage point, the cargo side of the cleavage point, or on both sides of the cleavage point. FIGS. 1, 5, 6, 11A, 12, and 15 provide examples of linkers, and any features or motifs of such linkers can be used or combined with other features or motifs of other linkers. The backbone atoms of the linkers can be C, N, O, P, S, or the like, and can include carbons and hetero atoms.

The endosomal disrupter (i.e., endosomal disrupting member) can be any of a variety of members that are pH sensitive so as to provide endosomal disruption at higher pH values closer to neutral compared to late or lysosomal pH values. As such, it is preferable for the endosomal disrupter to induce endosomal disruption at a pH from 7 to about 5.5, more preferably from 7 to 6, and most preferably from 7 to 6.25 or 6.5. Such a limited range of pH is beneficial to induce disruption in early/recycling endosomes before degradation of the cargo can occur.

In one embodiment, the endosomal disrupter can include at least one of a PC4 peptide, a PC4 peptide related sequence, a PC4 peptide variant that includes at least one D-amino acid, or a peptidomimetic, and combinations thereof. The PC4 peptide has an amino sequence of AcNH(SSAWWSYWP-PVA) (SEQ ID NO: 1). Typically, peptides consisting of native amino acids include only L-amino acids. However, D-amino acids can readily be included in synthetic peptides.

In the PC4 peptide, other nonpolar amino acids (G, A, V, L, I, M, F, W, P) can be exchanged with the nonpolar amino acids as long as the endosomal disruption functionality is retained. Also, polar amino acids (S, T, C Y, N Q) can be exchanged with the polar amino acids as long as the endosomal disruption functionality is retained.

A peptidomimetic is a small protein-like chain designed to mimic a peptide. Peptidomimetics typically arise from modification of an existing peptide in order to alter the molecule's properties. For example, they may arise from modifications to change the molecule's stability or biological activity. These modifications involve changes to the peptide that will not occur naturally, such as altered backbones (e.g., peptoids) and the incorporation of non-natural amino acids.

With regard to Compound 1 having the endosomal disruptor, other endosomal disruptors can be used instead. As such, the endosomal disruptor can be modified to create a series of analogues that replace each amino acid of Compound 1 with alanine (alanine screen) to identify critical residues in the peptide sequence. Also, isosteric analogues can be prepared (e.g. W to F, Y, H; Y to F, W, H). Based on the results obtained from alanine scanning, the PC4 sequence may be capable of being truncated both from the N-terminus and/or the C-terminus to create lower molecular weight endosome disruptors. Additionally, spacing can be created between the aromatic residues in the PC4 peptide (amino acid sequence: SSAW-WSYWPPVA (SEQ ID NO: 1) by insertion of glycine residues at these sites.

Additionally, the pH-dependent INF7 peptide (amino acid sequence: GLFEAIEGFIENGWEGMIDGWYG) (SEQ ID NO: 3), a engineered fragment of the membrane-lytic influenza hemagglutinin HA-2 protein can be used in place or in addition to PC4. The INF7 peptide can be analogued by substitutions such as those described for PC4.

In one embodiment, a method for introducing an exogenous cargo molecule into a cell using endocytosis can include: providing a system that undergoes cellular membrane trafficking, the system including at least one membrane binding element linked to an endosomal disrupting element and at least one membrane binding element linked through a selectively cleavable anionic linker to an exogenous cargo molecule; providing at least one target cell of interest; exposing the target cell to the cellular trafficking system, wherein the at least one membrane binding element is directly or indirectly (e.g., through a receptor or other surface protein) associated with the membrane, and the cellular trafficking system induces uptake into an endosomal compartment by endocytosis; disrupting the endosomal compartment while an early endosome or recycling endosome using the endosomal compartment disrupting element; and releasing the cargo molecule from the endosome and membrane binding element by selective cleavage of the cleavable anionic linker while the endosomal compartment is an early endosome or recycling endosome. The system can be a multi-component system as described herein or a platform that includes the endosomal compartment disrupting element being linked to the membrane binding element that is also linked through a selectively cleavable anionic linker to the cargo molecule.

In one embodiment, the delivery platform or system is configured to selectively release the cargo molecule into a specific cell type. For example, the membrane-binding element can be modified so that it will not associate with a particular membrane of a cell unless it is processed by a tissue- or cell-specific factor. Cholesterylamine derivatives containing certain basic amino acids or polyethylene glycol (PEG) are not internalized by endocytosis and remain on the cell surface. Such a derivative can be targeted to a specific cell type by making analogues that contain protease cleavable elements that can be cleaved by cell-specific proteases resulting in delivery to specific cell types. It may also be possible to target the membrane binding element to a specific cell types by adding motifs (e.g., folate, RGD peptides, etc) that bind certain cell types.

Using the rational described above, the means for targeting the specific cell type can include configuring the endosomal compartment disrupting element to be active only in the specific cell type. For example, the PC4 peptide could be modified to include a motif that blocks activity and activity of the PC4 peptide is restored by cleavage of the motif by a tissue-specific protease.

In one embodiment, the delivery platform or system for targeting the specific cell type can include configuring the cleavable linker that couples the exogenous cargo molecule to the membrane binding element such that it can only be cleaved in a specific cell type. For example, the cleavable linker could include a protease recognition motif that is recognized and cleaved by a tissue specific protease.

In another embodiment, the means for targeting the specific cell type can include configuring the cleavable linker that couples the exogenous cargo molecule to the membrane binding element such that it can cleaved by an external signal. Suitable examples of external signals that can cleave a cleavable linker include, but are not limited to, heat, i.e., thermolysis, photoexcitation, i.e., photolysis, or ultrasound, i.e., sonolysis.

There are approximately 210 specific cell types found in the human body and there are many more diseased cell types. Suitable examples of specific cell types include, but are not limited to, at least one of an epithelial cell, a hormone secreting cell, an extracellular matrix secretion cell, a contractile cell, a blood cell, an immune cell, a nerve cell, a pigment cell, a germ cell, a nurse cell, an interstitial cell, a cancerous cell, or a pre-cancerous cell, diseased cells thereof, and combinations thereof.

The platform and/or system can include the agent being a nucleic acid, such as an siRNA such that the platform and system can effect gene silencing in cells. As such, the siRNA can be coupled to the ligand through a selectively cleavable linker as described herein. The siRNA can be unmodified or modified with a 2' modification. Also, the siRNA can be modified by having an internucleotide linkage. The siRNA can be linked to the linker through the sense or antisense strand.

As used herein, the term "2' modification" is meant to refer to a chemical modification of a nucleotide that occurs at the second position atom. As such, the 2' modification can include the conjugation of a chemical modification group to the 2' carbon of the ribose ring of a nucleotide, or a nucleotide within an oligonucleotide or polynucleotide. Thus, a 2' modification occurs at the 2' position atom of a nucleotide.

As used herein, the term "antisense strand" is meant to refer to a polynucleotide or region of a polynucleotide that is at least substantially (e.g., about 80% or more) or 100% complementary to a target nucleic acid of interest. Also, the antisense strand of a dsRNA is complementary to its sense strand. An antisense strand may be comprised of a polynucleotide region that is RNA, DNA, or chimeric RNA/DNA. Additionally, any nucleotide within an antisense strand can be modified by including substituents coupled thereto, such as in a 2' modification. The antisense strand can be modified with a diverse group of small molecules and/or conjugates. For example, an antisense strand may be complementary, in whole or in part, to a molecule of messenger RNA ("mRNA"), an RNA sequence that is not mRNA including non-coding RNA (e.g., tRNA and rRNA), or a sequence of DNA that is either coding or non-coding. The terms "antisense strand" and "antisense region" are intended to be equivalent and are used interchangeably.

As used herein, the terms "complementary" and "complementarity" are meant to refer to the ability of polynucleotides to form base pairs with one another. Base pairs are typically formed by hydrogen bonds between nucleotide units in anti-parallel polynucleotide strands. Complementary polynucleotide strands can base pair in the Watson-Crick manner (e.g., A to T, A to U, C to G), or in any other manner that allows for the formation of duplexes in a duplex region. Persons skilled in the art are aware, when using RNA as opposed to DNA, uracil rather than thymine is the base that is considered to be complementary to adenosine.

Perfect complementarity or 100% complementarity refers to the situation in which each nucleotide unit of one polynucleotide strand can hydrogen bond with a nucleotide unit of an anti-parallel polynucleotide strand. Less than perfect complementarity refers to the situation in which some, but not all, nucleotide units of two strands can hydrogen bond with each other. For example, for two 20-mers, if only two base pairs on each strand can hydrogen bond with each other, the polynucleotide strands exhibit 10% complementarity. In the same example, if 18 base pairs on each strand can hydrogen bond with each other, the polynucleotide strands exhibit 90% complementarity. "Substantial complementarity" refers to polynucleotide strands exhibiting 79% or greater complementarity, excluding regions of the polynucleotide strands, such as overhangs, that are selected so as to be non-complementary. Accordingly, complementarity does not consider overhangs that are selected so as not to be similar or complementary to the nucleotides on the anti-parallel strand.

As used herein, the term "duplex region" is meant to refer to the region in two complementary or substantially complementary polynucleotides that form base pairs with one another, either by Watson-Crick base pairing or any other manner that allows for a stabilized duplex between the polynucleotide strands. For example, a polynucleotide strand having 21 nucleotide units can base pair with another polynucleotide of 21 nucleotide units, yet only 19 bases on each strand are complementary such that the "duplex region" has 19 base pairs. The remaining bases may, for example, exist as 5' and/or 3' overhangs. Further, within the duplex region, 100% complementarity is not required, and substantial complementarity is allowable within a duplex region. Substantial complementarity refers to 79% or greater complementarity and can result from mismatches and/or bulges. For example, a single mismatch in a duplex region consisting of 19 base pairs results in 94.7% complementarity, rendering the duplex region substantially complementary.

As used herein, the term "gene silencing" is meant to refer to a process by which the expression of a specific gene product is inhibited by being lessened, attenuated, and/or terminated. Gene silencing can take place by a variety of pathways. In one instance, gene silencing can refer to a decrease in gene product expression that results from the RNAi pathway, wherein an siRNA acts in concert with host proteins (e.g., RISC) to degrade mRNA in a sequence-dependent manner. Alternatively, gene silencing can refer to a decrease in gene product expression that results from siRNA mediated translation inhibition. In still another alternative, gene silencing can refer to a decrease in gene product expression that results from siRNA mediated transcription inhibition. The level of gene silencing can be measured by a variety of methods, which can include measurement of transcript levels by Northern Blot Analysis, B-DNA techniques, transcription-sensitive reporter constructs, expression profiling (e.g., DNA chips), and related technologies and assays. Alternatively, the level of gene silencing can be measured by assessing the level of the protein encoded by a specific gene that is translated from the corresponding mRNA. This can be accomplished by performing a number of studies including Western Analysis, measuring the levels of expression of a reporter protein, such as colorimetric or fluorescent properties (e.g., GFP), enzymatic activity (e.g., alkaline phosphatases), or other well known analytical procedures.

As used herein, the term "internucleotide linkage" is meant to refer to the type of bond or link that is present between two nucleotide units in a polynucleotide, wherein the linkage may be modified or unmodified. The phrase "modified internucleotide linkage" includes all modified internucleotide linkages now known or later developed. Internucleotide linkages may have associated counterions, and the phrase is meant to include such counterions and any coordination complexes that can form at the internucleotide linkages.

As used herein, the term "sense strand" is meant to refer to a polynucleotide or region that has the same nucleotide sequence, in whole or in part, as a target nucleic acid such as a messenger RNA or a sequence of DNA. The term "sense strand" includes the sense region of a polynucleotide that forms a duplex with an antisense region of another polynucleotide. Also, a sense strand can be a first polynucleotide sequence that forms a duplex with a second polynucleotide sequence on the same unimolecular polynucleotide that includes both the first and second polynucleotide sequences. As such, a sense strand can include one portion of a unimolecular siRNA that is capable of forming hairpin structure, such as an shRNA. When a sequence is provided, by convention, unless otherwise indicated, it is the sense strand or region, and the presence of the complementary antisense strand or region is implicit. The phrases "sense strand" and "sense region" are intended to be equivalent and are used interchangeably.

As used herein, the term "siRNA" is meant to refer to a small inhibitory RNA duplex that induces gene silencing by operating within the RNA interference ("RNAi") pathway. These siRNA are dsRNA that can vary in length, and can contain varying degrees of complementarity between the antisense and sense strands, and between the antisense strand and the target sequence. Each siRNA can include between 17 and 31 base pairs, more preferably between 18 and 26 base pairs, and most preferably 19 and 21 base pairs. Some, but not all, siRNA have unpaired overhanging nucleotides on the 5' and/or 3' end of the sense strand and/or the antisense strand. Additionally, the term "siRNA" includes duplexes of two separate strands, as well as single strands that can form hairpin structures comprising a duplex region, which may be referred to as short hairpin RNA ("shRNA").

As used herein, the term "target" is used in a variety of different forms throughout this document and is defined by the context in which it is used. The term "target gene" is meant to refer to the gene that encodes the protein to be silenced by the siRNA, and encodes for the production of the target mRNA. The term "target mRNA" is meant to refer to an mRNA against which a given siRNA is direct to silence the transcription of the polypeptide product. The term "target sequence" and "target site" are meant to refer to a sequence within the mRNA, miRNA, or DNA coding or promoter region to which the sense strand of an siRNA exhibits varying degrees of homology and the antisense strand exhibits varying degrees of complementarity. The term "target polypeptide" or "target protein" is meant to refer to the gene product encoded by the target gene, target mRNA, and/or target sequence. The term "siRNA target" can refer to the gene, mRNA, or protein against which the siRNA is directed to for silencing. Similarly, "target silencing" can refer to the state of silencing a gene, or the corresponding mRNA or protein.

Additional information regarding nucleic acids, RNA, siRNA, modifications, and formulations thereof can be found in Tuschl et al. (US 2004/0229266), Giese et al. (US 2004/0180351), McSwiggen et al. (US 2003/0170891), and Bartelmez et al. (U.S. Pat. No. 6,841,542), which are incorporated herein by specific reference.

The present invention may be embodied in other specific forms without departing from its spirit or essential characteristics. The described embodiments are to be considered in all respects only as illustrative and not restrictive. The scope of the invention is, therefore, indicated by the appended embodiments rather than by the foregoing description. All changes which come within the meaning and range of equivalency of the embodiments are to be embraced within their scope. All references recited herein are incorporated herein by specific reference in their entirety.

EXPERIMENTAL

Synthesis of novel delivery platforms and systems are capable of entering a cell via endocytosis and capable of having the cargo selectively escape from early/recycling endosomes of living mammalian cells. Because these endosomes are less acidic and less hydrolytically active than late endosomes/lysosomes, this approach may be advantageous when compared to delivery methods that penetrate deeper into the endosomal system. To selectively deliver compounds into early/recycling endosomes, we synthesized four derivatives of the dynamic membrane anchor N-alkyl-3β-cholesterylamine (Peterson, B. R. Org. Biomol. Chem. 2005, 3, 3607-3612; Boonyarattanakalin, S.; Hu, J.; Dykstra-Rummel, S. A.; August, A.; Peterson, B. R. J. Am. Chem. Soc. 2007, 129, 268-269) (Compounds 1-4) as shown in FIG. 1. Two of these compounds (Compound 1, and red fluorescent Compound 2) incorporate PC4, a pH-dependent membrane-lytic dodecapeptide previously reported (Hirosue, S.; Weber, T. Biochemistry 2006, 45, 6476-6487) to disrupt membranes of liposomes. Two others comprise the green fluorophore 5-carboxyfluorescein linked through disulfide (Compound 3) and amide (Compound 4) bonds. The unmodified PC4 peptide with the amino acid sequence AcNH(SSAWWSYWPP-VA)CONH$_2$ (Compound 5) (SEQ ID NO: 1) was additionally prepared as a control.

Figure 2A:
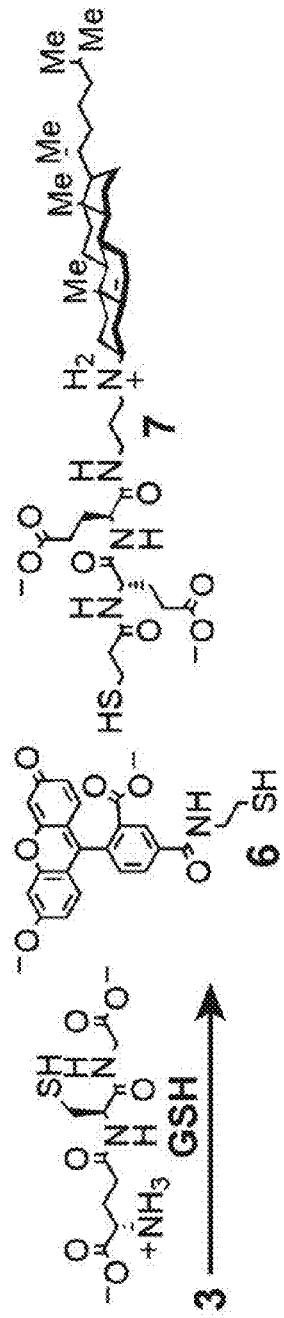
FIG. 2A shows cleavage of the disulfide linker of Compound 3 with GSH.
Figure 2B:
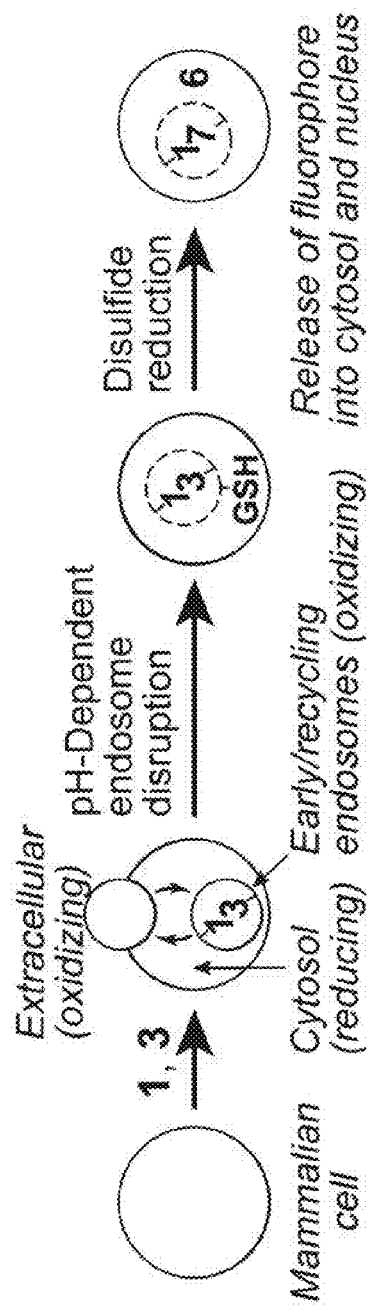
FIG. 2B shows a schematic of a strategy for the selective release of disulfide-tethered cargo from membranes of early/recycling endosomes mediated by Compound 1 or Compound 2.

When added to mammalian cells, derivatives of N-alkyl-3β-cholesterylamine have been shown to become avidly incorporated in cellular plasma membranes and engage a membrane trafficking pathway that involves rapid cycling between the cell surface and intracellular endosomes, similar to many natural cell surface receptors. The partitioning of these compounds between the plasma membrane and early/recycling endosomes is affected by the structure of the linker region proximal to the membrane anchor (Boonyarattanakalin, S.; Martin, S. E.; Dykstra, S. A.; Peterson, B. R. *J. Am. Chem. Soc.* 2004, 126, 16379-16386). In Compounds 1-4, the glutamic acid residue(s) in this region were installed to enhance the binging to a receptor and increase localization of these compounds in endosomes compared to the plasma membrane. The acidic residues, which can be substituted with other acidic moieties or other anionic moieties can also facilitate enhanced endocytosis. Because early/recycling endosomes are thought to be oxidizing, (Austin, C. D.; Wen, X.; Gazzard, L.; Nelson, C.; Scheller, R. H.; Scales, S. J. *Proc. Natl. Acad. Sci. U.S.A.* 2005, 102, 17987-17992), the delivery platform and system were configured to include a cleavable disulfide linker, as shown in Compound 3, should be relatively stable in these compartments. However, when Compound 3 is exposed to reduced glutathione (GSH), a thiol present at mM concentrations in the cytosol, this disulfide linker would be cleaved (FIG. 2A) (Saito, G.; Swanson, J. A.; Lee, K. D. *Adv. Drug Deliv. Rev.* 2003, 55, 199-215). Correspondingly, disruption of early/recycling endosomes loaded with Compound 3 can be accomplished with Compounds 1 or 2 so as to enable GSH to access these compartments, reduce the disulfide of Compound 3, and release the soluble fluorophore Compound 6 into the cytoplasm and nucleus of cells (see, FIG. 2B). The same principle can be applied to agents for delivery into cells instead of the fluorophore.

Figure 3A:
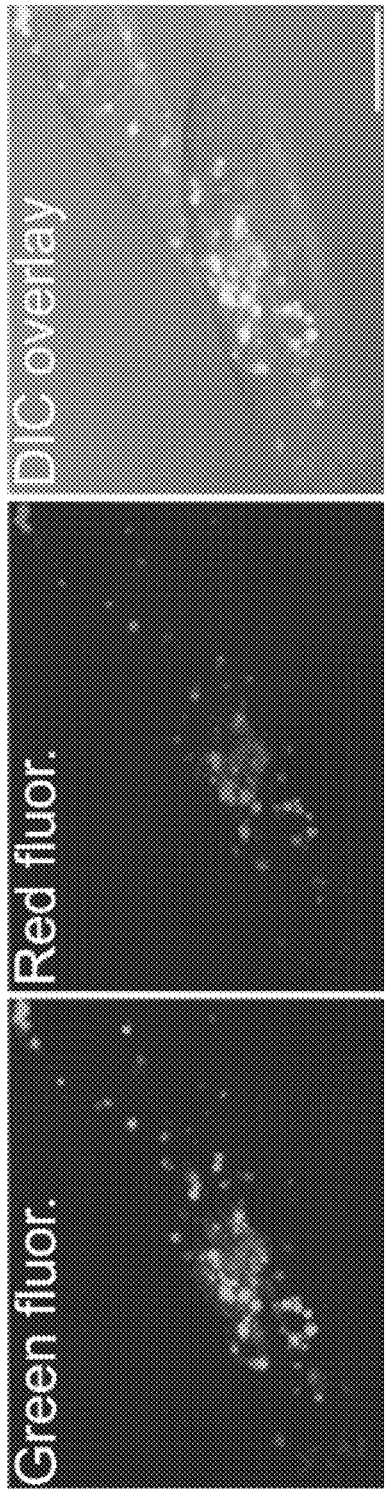
FIGS. 3A-3B show confocal laser scanning and differential interference contrast (DIC) micrographs of living CHO cells treated with green fluorescent 3 (5 µM) for 12 h followed by red fluorescent Texas Red transferrin (FIG. 3A, 500 nM) or DiI-LDL (FIG. 3B, 8 nM) for 5 min. Colocalization of red and green fluorescence is shown as yellow pixels in the DIC overlay images. Arrows point to distinct red fluorescence.
Figure 3B:
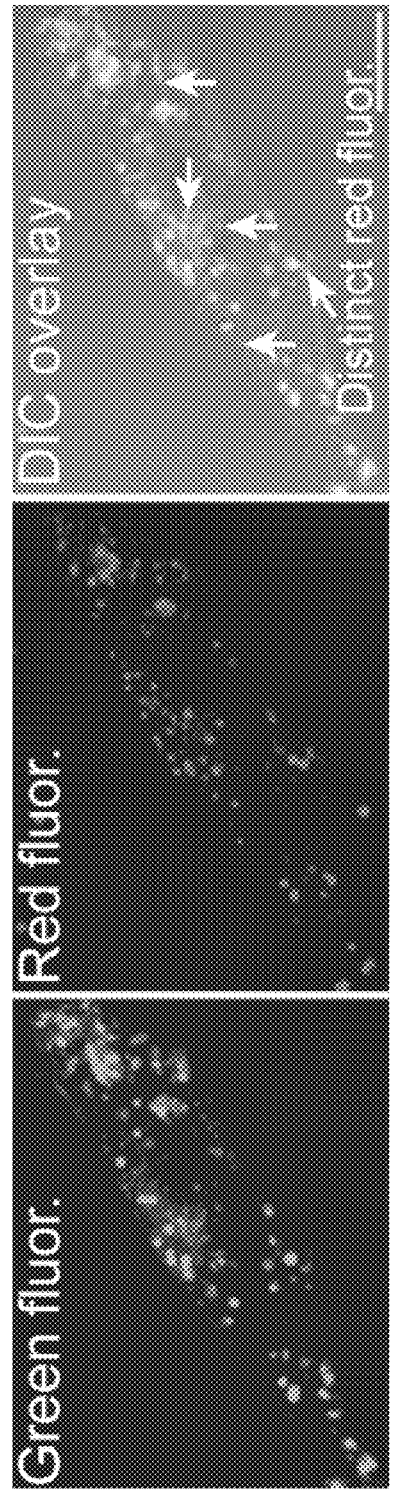

Confocal laser scanning microscopy was employed to examine the subcellular localization of fluorescent compounds of the delivery system added to living mammalian cells. In Chinese hamster ovary (CHO) cells, Compound 3 was found to become localized in defined intracellular compartments that reside outside of the cell nucleus (FIGS. 3A-3B). These compartments were identified as early/recycling endosomes by essentially complete intracellular colocalization with red fluorescent transferrin protein, a highly selective marker (Sheff, D.; Pelletier, L.; O'Connell, C. B.; Warren, G.; Mellman, I. *J. Cell. Biol.* 2002, 156, 797-804). As a control, cells were similarly treated with red fluorescent DiI-labeled low density lipoprotein (LDL), a protein that selectively accumulates in late endosomes and lysosomes (Ghosh, R. N.; Gelman, D. L.; Maxfield, F. R. *J. Cell Sci.* 1994, 107, 2177-2189). Treatment with DiI-LDL revealed distinct red fluorescence, establishing that in this cell line the N-alkyl-3β-cholesterylamine membrane anchor promotes delivery of the fluorophore of Compound 3 to early/recycling endosomes with a high level of specificity. As such, it is expected that N-alkyl-3β-cholesterylamine similarly correlate with the early/recycling endosomes that have higher pH values than late endosomes or lysosomes.

Figure 4A:
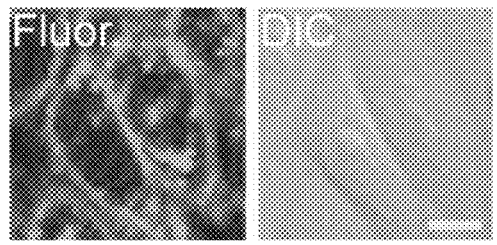
FIG. 4A-4J show confocal fluorescence and DIC micrographs of living cells treated with fluorescent probes.
Figure 4B:
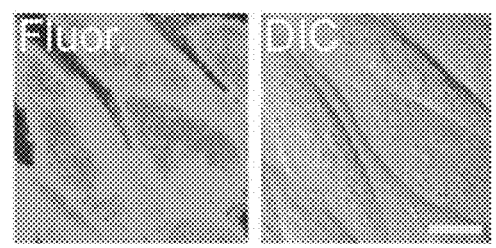
Figure 4C:
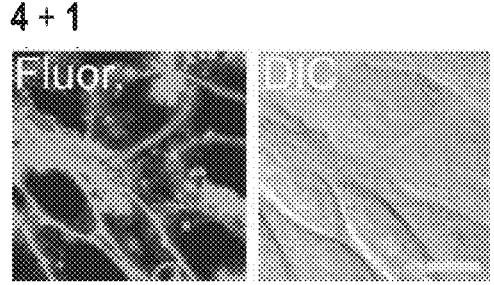
Figure 4D:
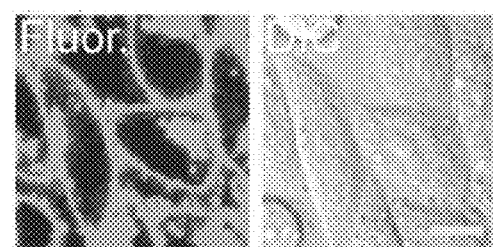
Figure 4E:
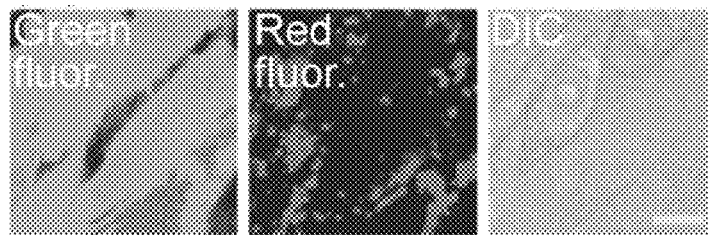
Figure 4F:
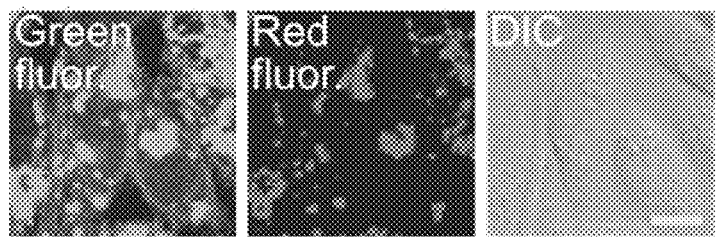
Figure 4G:
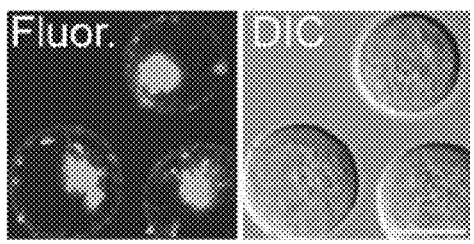
Figure 4H:
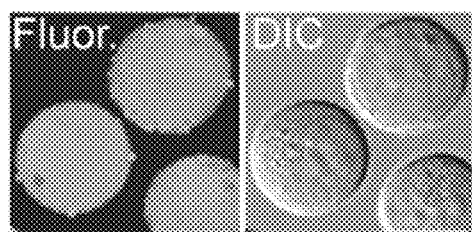
Figure 4I:
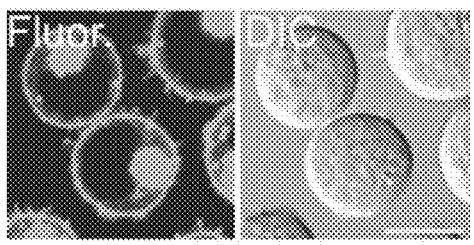
Figure 4J:
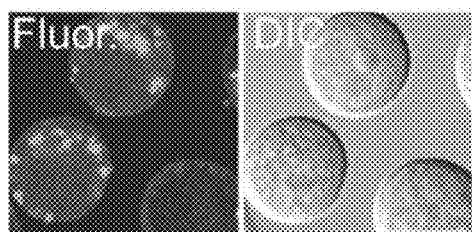
Figure 4K:
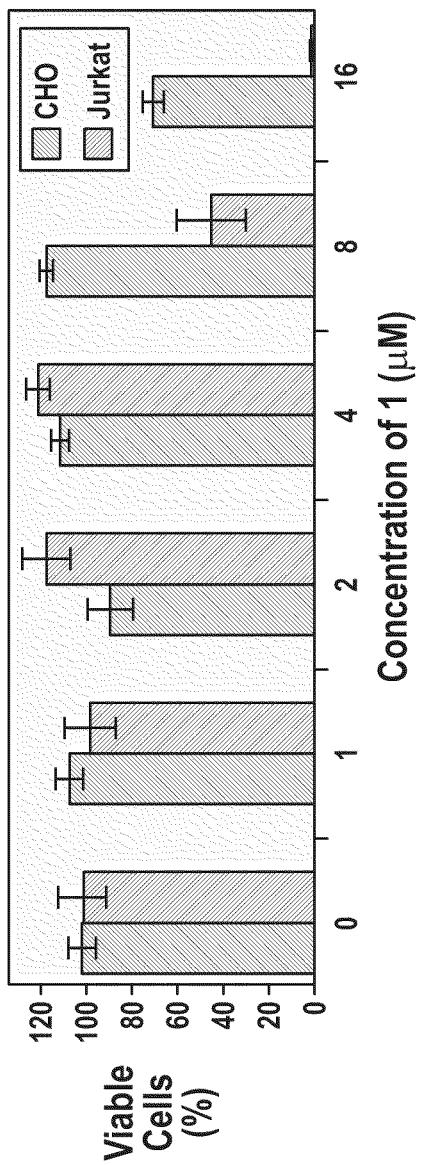
FIG. 4K shows the toxicity to CHO and Jurkat cells after incubation with Compound 1 for 48 h at 37° C.
Figure 5:
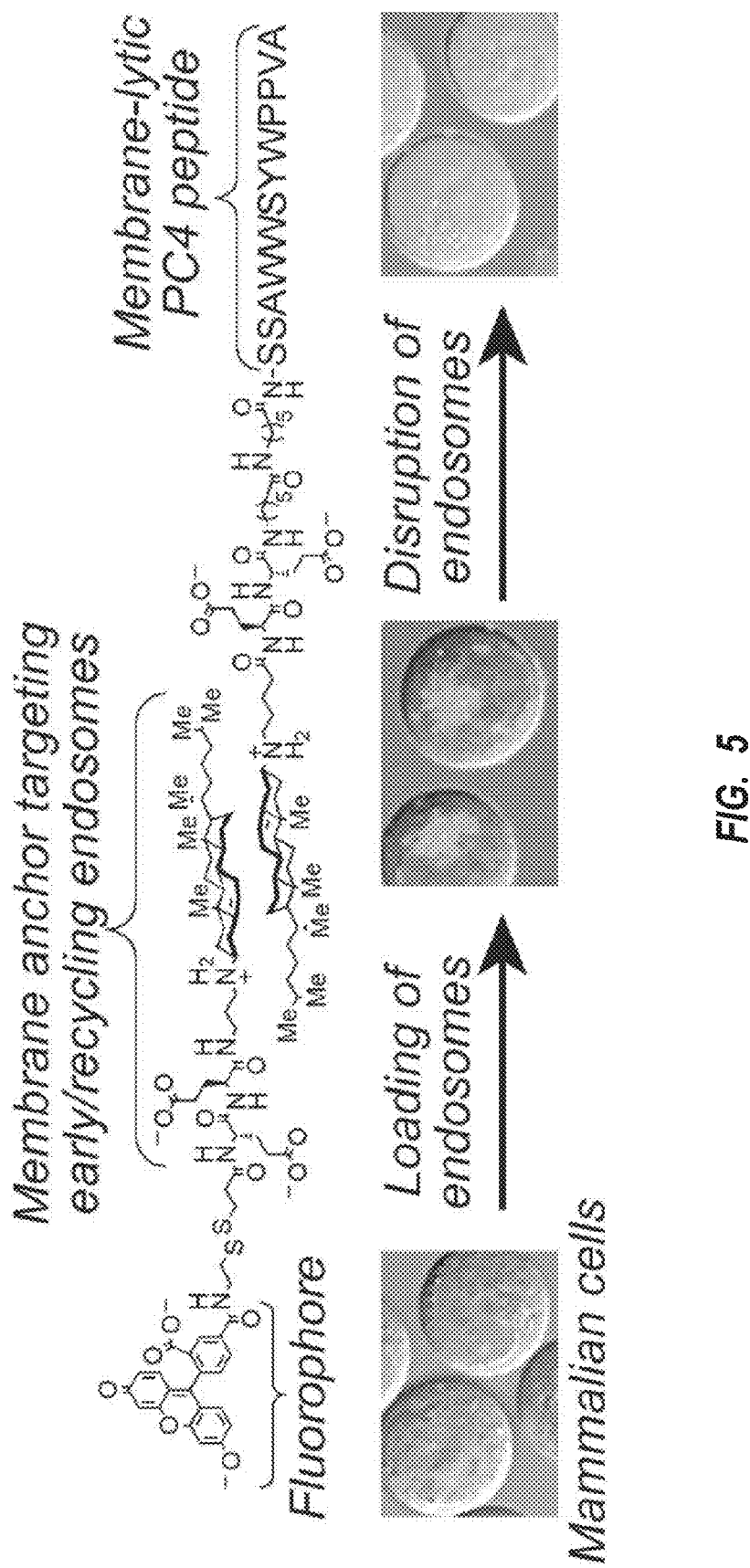
FIG. 5 is a schematic representation of mammalian cells without any delivery system, endosomal localization of the delivery system, followed by endosomal release of the delivery system. PC4 peptide disclosed as SEQ ID NO: 1. Full length compound disclosed as SEQ ID NO: 2.
Figure 6:
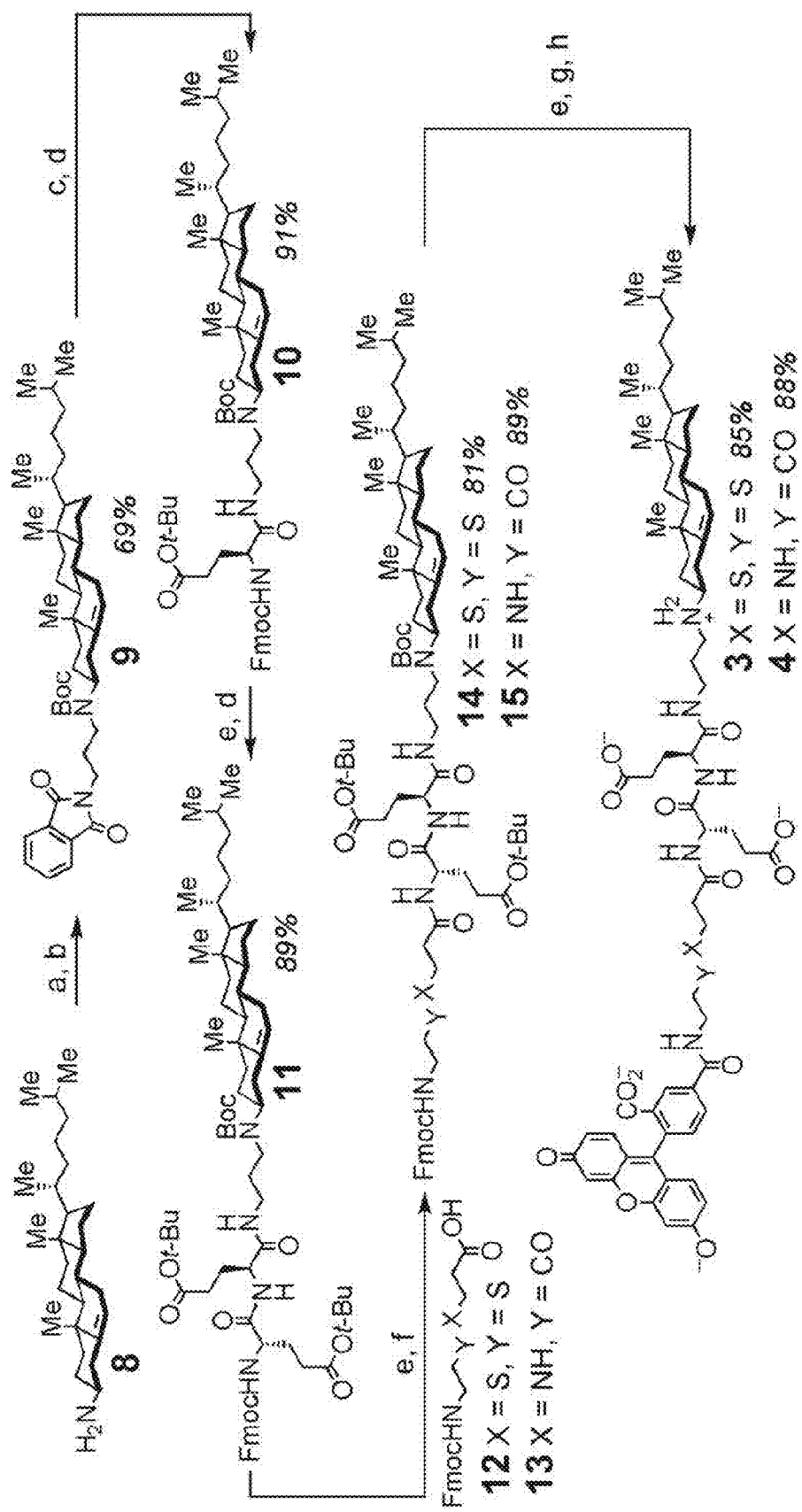
FIG. 6 is a schematic representation of the synthesis of Compounds 3 and 4. Reagents and conditions: (a) N-3-bromopropyl phthalimide, $K_2CO_3$, DMF, 60° C., 24 h; (b) $(Boc)_2$O, DIEA, $CH_2Cl_2$, 4 h; (c) $NH_2NH_2$, EtOH, 50° C., 4 h; (d) EDC, HOBt, Fmoc-Glu(Ot-Bu)-OH, 4° C. to 22° C., 12 h; (e) 20% piperidine, DMF, 30 min; (f) EDC, HOBt, Compound 12 or Compound 13, 4° C. to 22° C., 12 h; (g) 5-carboxyfluorescein, succinimidyl ester, DIEA, DMF, 12 h; (h) 20% TFA, $CH_2Cl_2$, 12 h.

Compared to Compound 3 alone, living cells treated with both Compound 3 and Compound 1 (or Compound 2) showed a strikingly different pattern of intracellular fluorescence (FIG. 4A-4J). When combined with Compound 1 or Compound 2, the green fluorescence of Compound 3 was released from entrapment in early/recycling endosomes and fluorescence was observed in the cytosol and nucleus. As shown in FIGS. 4A-4J, this release of fluorescent cargo from endosomal membranes was effective in both adherent cells (CHO) and suspension cells (human Jurkat lymphocytes). Consistent with the model shown in FIG. 2B, replacement of the disulfide of Compound 3 with the amide bond of Compound 4 blocked release of the fluorophore (FIGS. 4C and 4I). The red fluorescence of Compound 2 allowed visualization of the linked PC4 peptide in early/recycling endosomes. Colocalization of Compound 1 or Compound 2 with Compound 3 in these compartments was required to promote efficient cargo release; little effect was observed with the unmodified PC4 peptide (Compound 5) (SEQ ID NO: 1). While the invention has been proven to be functional with the system, a platform that includes a single N-alkyl-3β-cholesterylamine linked to an early/recycling endosomal disrupter and also linked through a selectively cleavable anionic linker to a cargo molecule would also be similarly functional.

Figure 7:
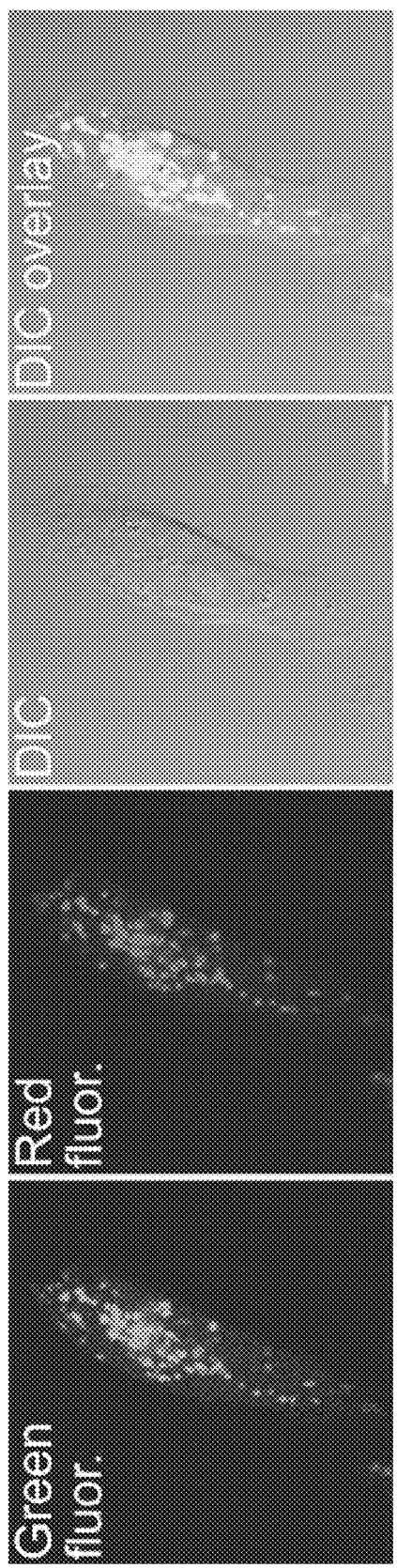
FIG. 7 shows confocal and DIC micrographs of CHO cells treated with Compound 2 and a transferrin Alexa Fluor 488 conjugate. Cells were treated with red fluorescent Compound 2 (5 µM) for 12 h followed by addition of the green fluorescent transferrin conjugate (610 nM) for 5 min. Cells were washed with media and imaged by differential interference contrast (DIC) and confocal laser scanning microscopy. Essentially complete colocalization of red and green fluorescence was observed, indicating that Compound 2 becomes selectively localized in early/recycling endosomes.

As shown in FIG. 7, confocal and DIC micrographs were generated for CHO cells that were treated with Compound 2 and a transferrin Alexa Fluor 488 conjugate. Cells were treated with red fluorescent 2 (5 µM) for 12 h followed by addition of the green fluorescent transferrin conjugate (610 nM) for 5 min. Cells were washed with media and imaged by differential interference contrast (DIC) and confocal laser scanning microscopy. Essentially complete colocalization of red and green fluorescence was observed, indicating that Compound 2 becomes selectively localized in early/recycling endosomes.

Figure 8:
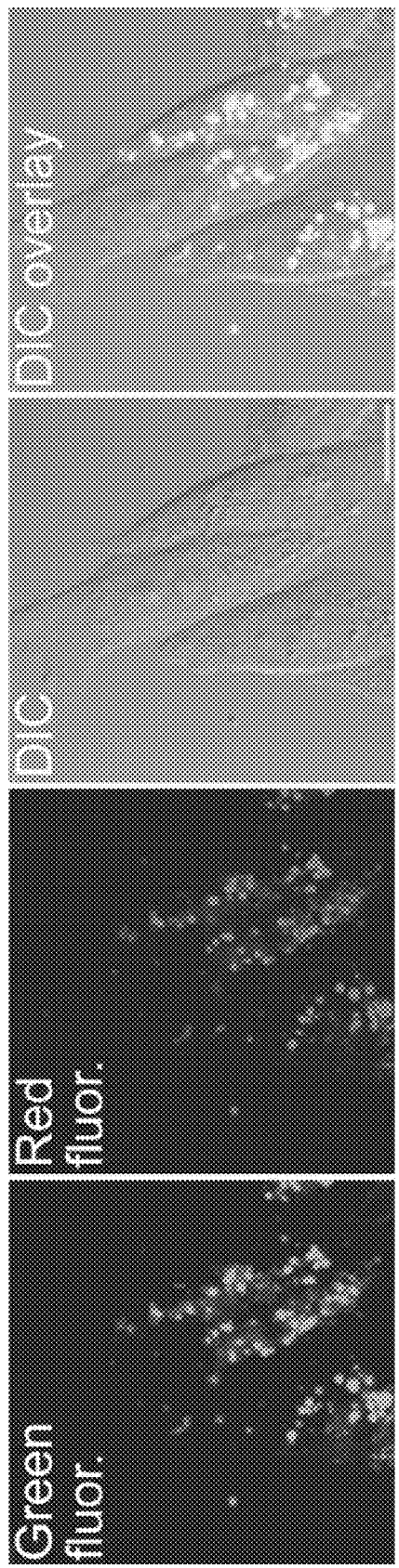
FIG. 8 shows confocal and DIC micrographs of CHO cells treated with Compounds 2 and 3 under conditions that minimally disrupt endosomes. Cells were treated with red fluorescent Compound 2 (2 µM) and green fluorescent Compound 3 (5 µM) for 12 h. Cells were washed with media and imaged by DIC and confocal laser scanning microscopy. Essentially complete colocalization of red and green fluorescence in early/recycling endosomes was observed.

As shown in FIG. 8, confocal and DIC micrographs were generated for CHO cells treated with Compound 2 and Compound 3 under conditions that minimally disrupt endosomes. Cells were treated with red fluorescent Compound 2 (2 µM) and green fluorescent Compound 3 (5 µM) for 12 h. Cells were washed with media and imaged by DIC and confocal laser scanning microscopy. Essentially complete colocalization of red and green fluorescence in early/recycling endosomes was observed.

To investigate the importance of endosomal acidity on the function of the PC4 peptide, we increased endosomal pH by adding chloroquine (Adachi, K.; Ichinose, T.; Takizawa, N.; Watanabe, K.; Kitazato, K.; Kobayashi, N. *Arch. Virol.* 2007, 152, 2217-2224) and bafilomycin A1 (Yoshimori, T.; Yamamoto, A.; Moriyama, Y.; Futai, M.; Tashiro, Y. *J. Biol. Chem.* 1991, 266, 17707-17712). These compounds blocked release of the fluorophore (FIGS. 4E and 4F), consistent with the pH-dependent membrane-lytic activity of PC4. Because the acidity of endosomes is required for efficient membrane disruption, deleterious effects of Compound 1 and Compound 2 on the plasma membrane, which is surrounded by media of pH 7.4, should be limited. Consistent with this, assays of cellular viability (FIG. 4J) revealed that Compound 1 is nontoxic under conditions that disrupt early/recycling endosomes in CHO cells (8 µM) or Jurkat lymphocytes (2 µM).

Figure 9A:
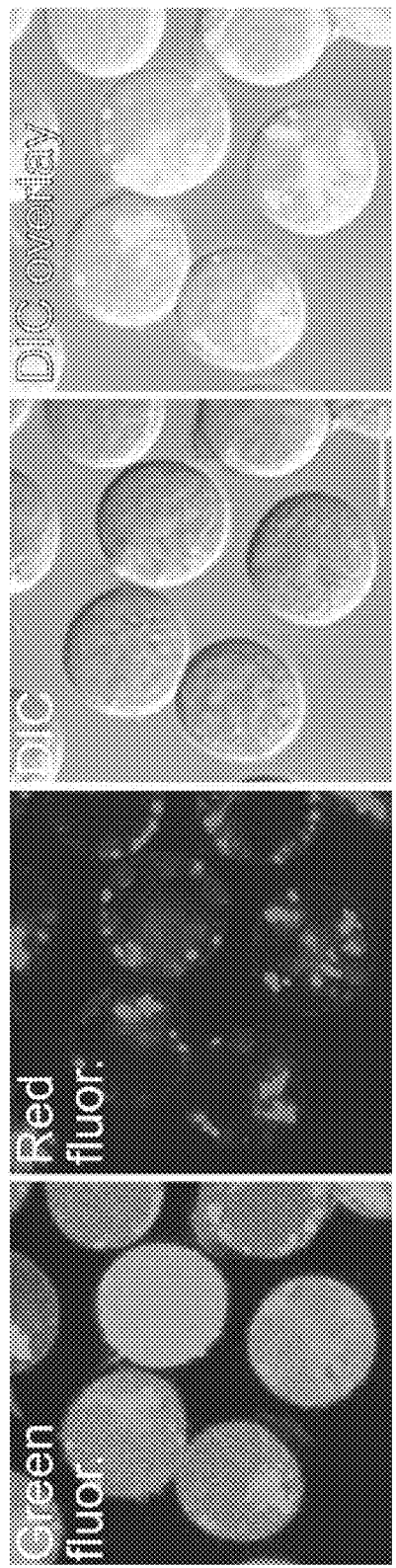
FIG. 9A-9B show inhibition of endosomal escape in Jurkat lymphocytes with bafilomycin A1. Jurkat cells were treated with green fluorescent Compound 3 (2.5 µM) and red fluorescent Compound 2 (2 µM) for 12 h at 37° C.
Figure 9B:
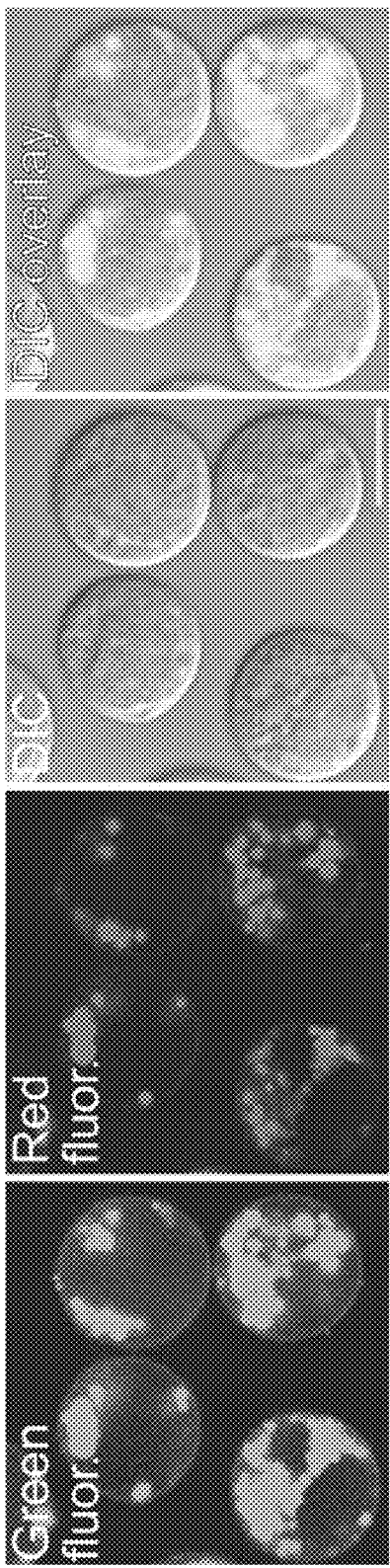

FIG. 9A-9B show inhibition of endosomal escape in Jurkat lymphocytes with bafilomycin A1. Jurkat cells were treated with green fluorescent Compound 3 (2.5 µM) and red fluorescent Compound 2 (2 µM) for 12 h at 37° C. In FIG. 9B, bafilomycin A1 (1 µM), a vacuolar H$^+$ ATPase inhibitor that blocks acidification of endosomes, was added. Cells were washed with media and imaged by DIC and confocal laser scanning microscopy. FIG. 9A shows endosomal escape, while FIG. 9B shows retention in endosomes. Thus, endosomal escape is pH dependent.

Figure 10A:
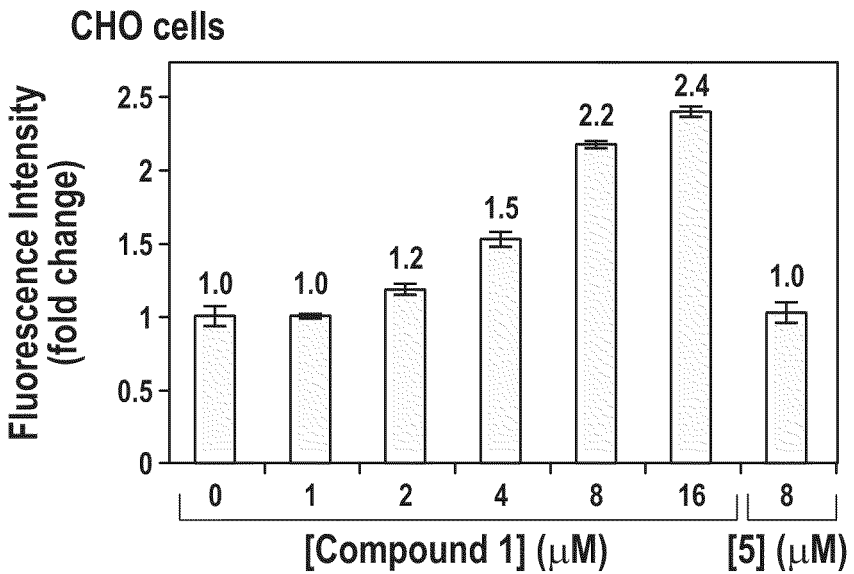
FIG. 10A-10B show graphs of dose dependence of endosomal escape quantified by flow cytometry.
Figure 10B:
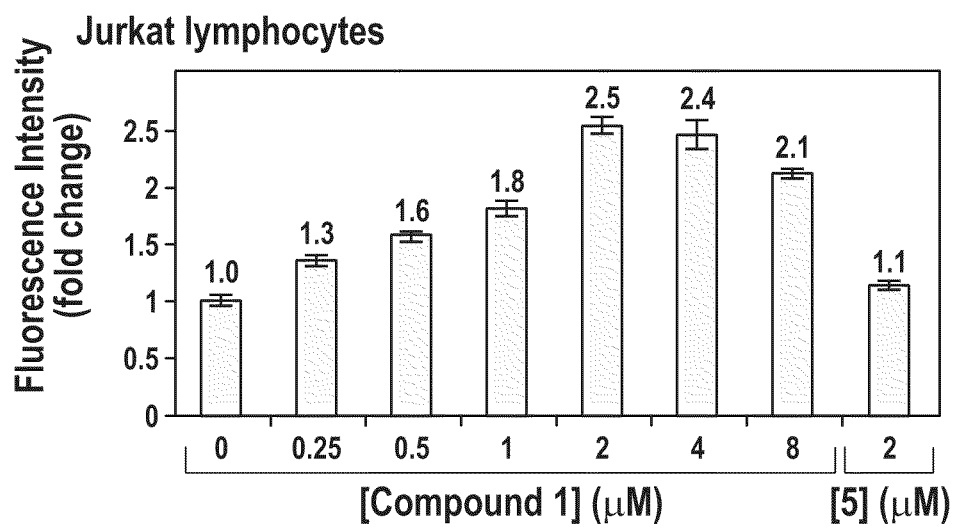

FIGS. 10A and 10B show that increasing the amount of the endosomal disrupter in the system can increase the amount of cargo in the cell. As shown in both CHO and Jurkat cells, the increased amounts of Compound 1 increased fluorescence. In contrast, the free endosomal disrupter (Compound 5) did not increase fluorescence at an equivalent amount of 8 micromolar.

Thus, the ability of N-alkyl-3β-cholesterylamines to specifically target a subset of relatively non-hydrolytic early/recycling endosomes and release selectively cleavable linker-linked (e.g., disulfide-linked) cargo from these compartments may be advantageous for a variety of cellular delivery applications to deliver the cargo molecule.

Figure 11A:
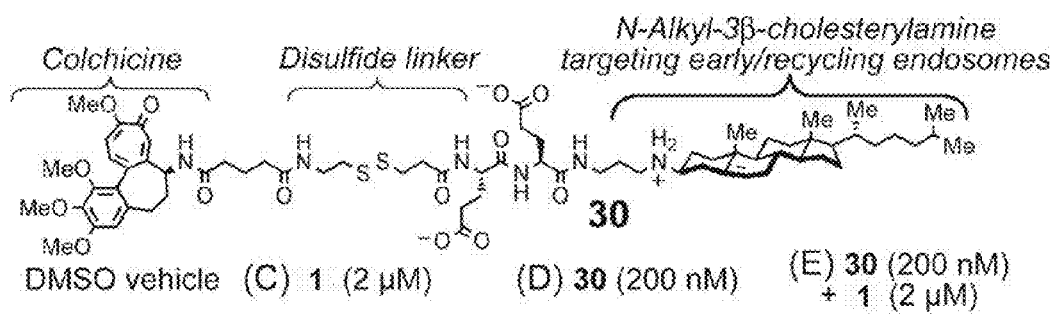
FIG. 11A shows a structure of a delivery platform having a cleavable disulfide-linked colchicine-cholesterylamine (Compound 30).
Figures 11B, 11C:
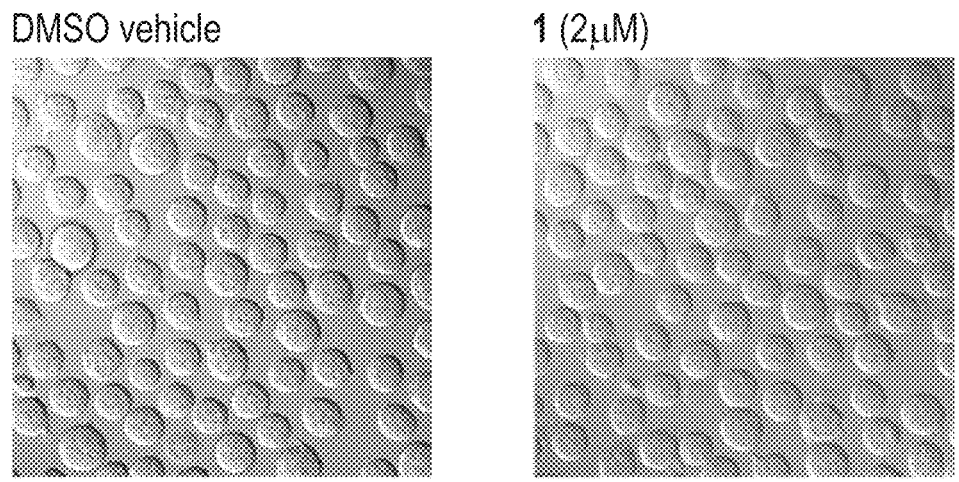
FIGS. 11B-11E show DIC micrographs of Jurkat lymphocytes treated for 48 h with DMSO (FIG. 11B), Compound 1 (FIG. 11C), Compound 30 (FIG. 11D, and Compounds 1 and 30 (FIG. 11E).
Figures 11D, 11E:
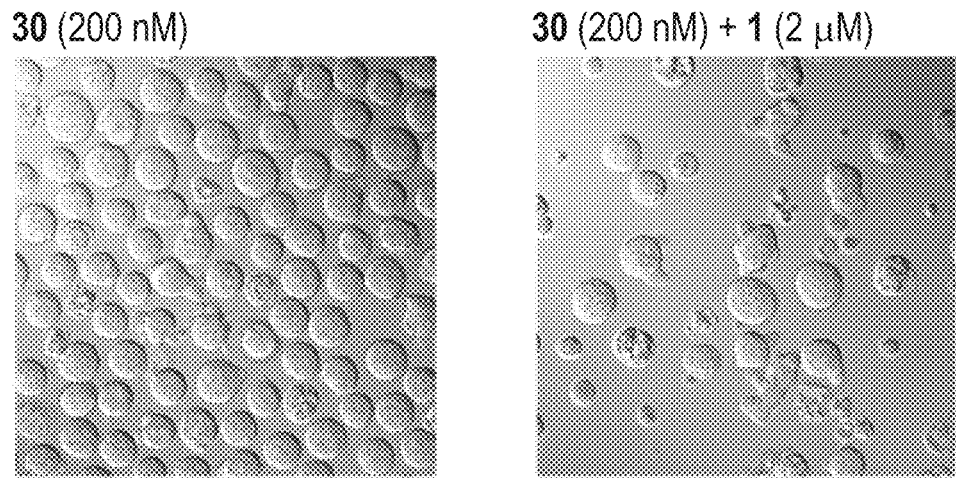

The delivery system was studied with the anticancer agent colchicine being linked to the N-alkyl-3β-cholesterylamine via a disulfide, which compound is Compound 30 as shown in FIG. 11A. The delivery system utilized Compound 1 to release the anticancer agent colchicine from Compound 30. Colchicine was linked to an N-alkyl-3β-cholesterylamine via a disulfide linker to present a compound that is non-toxic to Jurkat lymphocytes at 200 nM. The cholesterylamine-PC4 peptide (Compound 1) is similarly non-toxic at 2 μM. However, the combination of these two compounds (Compound 1+Compound 30) is lethal to lymphocytes because Compound 1 enables release of the toxic colchicine derivative (FIGS. 11B-11E). This result provides evidence that breaking a bond between N-alkyl-3β-cholesterylamine and an antimitotic agent can be used to control anticancer activity. It is thought that tumor-specific proteases capable of cleaving a peptide bond linking N-alkyl-3β-cholesterylamines to doxorubicin or other cancer agent will similarly enable the specific delivery of drugs to cognate cancer cells. Also, a cell type specific protease can be used for controlling delivery of the agent into the cytosol of those cell types.

Diverse proteases are found in every tissue of vertebrates, but most proteases are compartmentalized in lysosomes (e.g. cathepsins) or other intracellular compartments such as the cytoplasm (examples include the proteasome and caspases). Proteases found in the cytoplasm can be used for cleaving a linker having a corresponding substrate for cleavage. On the other hand, proteases localized exclusively in the lysosome are not considered for this invention. A limited subset of the degradome (the total complement of proteases expressed in vivo) is found in the extracellular environment, on cell surfaces, or in early/recycling endosomes. Because of the restricted localization of cholesterylamines, metastatic cancer cells that overexpress extracellular tumor specific proteases such as MMP-2, have the potential to selectively cleave a peptide bond linking N-alkyl-3β-cholesterylamines to anti-cancer agents.

Figure 12:
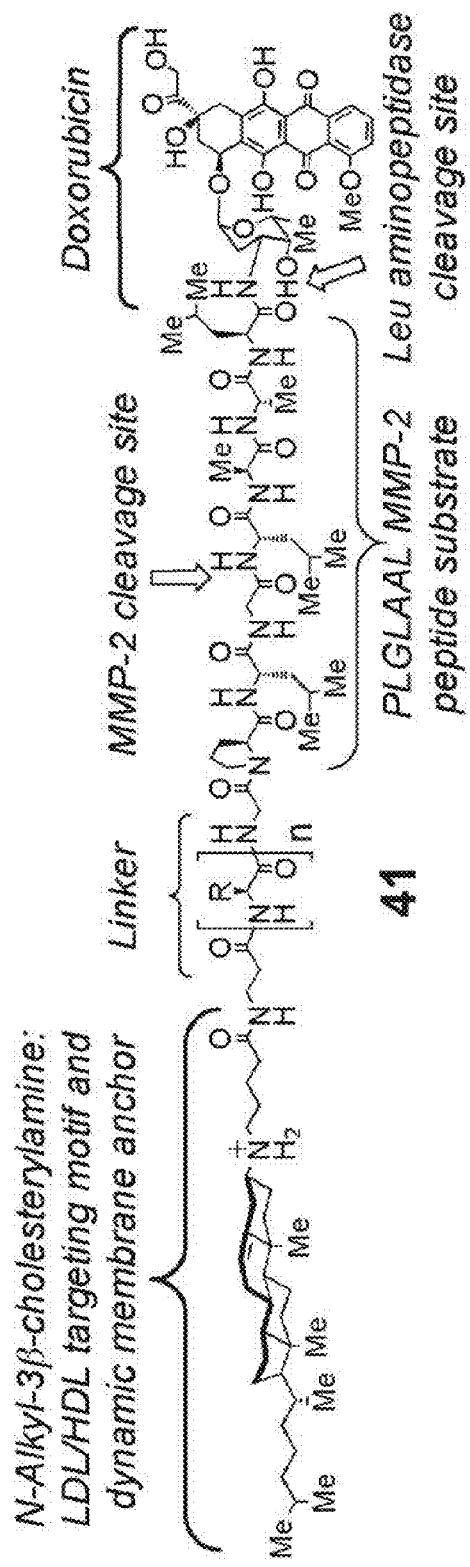
FIG. 12 shows the structure of a covalent drug delivery system (41) designed to be activated by tumor-specific proteases by having a MMP-2 cleavable substrate ('PLGLAAL' disclosed as SEQ ID NO: 4). Compound 41 disclosed as SEQ ID NO: 9.

To pursue this objective, a delivery system was prepared by doxorubicin covalently linked to N-alkyl-3β-cholesterylamines through an MMP-2 peptide substrate (Compound 41 of FIG. 12). The peptide substrate is the amino acid sequence PLGLAAL (SEQ ID NO: 4). Briefly, Compound 41 can be synthesized by solid phase peptide synthesis using hyper-acid labile 2-chlorotrityl resin, which allows cleavage of the C-terminal carboxylate from the resin upon treatment with acetic acid without cleavage of other acid-labile (Boc, t-Bu ester) protecting groups. Subsequent conversion to a C-terminal NHS ester can be followed by cleavage of other acid-labile protecting groups (the steroidal 3β-NHR group of cholesterylamines is too sterically-hindered to react with NHS esters). This NHS ester will be coupled to the doxorubicin amino sugar in the final step of the synthesis. The structure of the linker region of Compound 41 can initially include one or more glutamic acid residues (or other anionic moiety as described herein) since these residues are known to improve the bioactivity of cholesterylamines. Examination of X-ray structures of the MMP-2 catalytic domain suggests that installation of one through a few protease-resistant beta-alanine residues that separate the protease substrate from the membrane anchor may be sufficient for efficient cleavage of the substrate. However, the optimal linker length of compounds such as Compound 41 can be determined empirically through synthesis of a variety of linker lengths and analysis of the kinetics of cleavage of these compounds using MMP-2 (Sigma) or MMP-2 purified from the supernatant of BeWo cells. The linker length or configuration can be similar as described herein.

Because N-alkyl-3β-cholesterylamines appear to mimic free cholesterol, in normal cells Compound 41 can be delivered to early/recycling endosomes. This restricted trafficking can allow the linked doxorubicin to be relatively non-toxic by blocking access to its targets: DNA and topoiosomerase II, in the nucleus. However, when added to metastatic cancer cells that express either the soluble or membrane-bound forms of MMP-2, the MMP-2 substrate of Compound 41 can be cleaved, releasing doxorubicin attached to a short peptide tag. This cleavage product is structurally similar to the doxorubicin derivative DTS-201, and should be similarly hydrolyzed by cytosolic Leu-aminopeptidase, liberating free doxorubicin.

Figure 13:
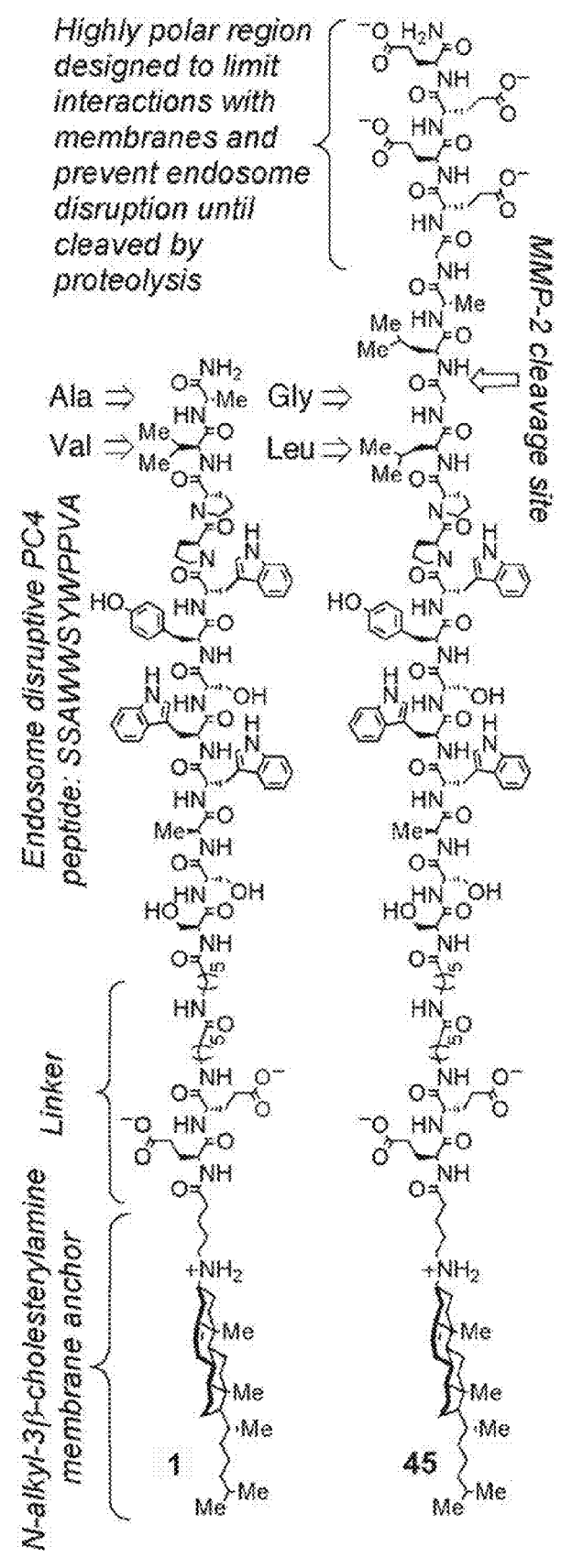

Another cholesterylamine linked PC4 conjugate designed to unleash endosome disruption activity upon cleavage by MMP-2 is shown in FIG. 13. In this embodiment, a highly polar GluGluGluGlu (SEQ ID NO: 5) region was added to the C-terminus of PC4 to prevent the interaction of this compound with endosomal membranes. Additionally, an MMP-2 cleavage site was added by the subtle change of ValAla at the C-terminus to LeuGly at the C-terminus. Cleavage by MMP-2 is designed to unmask an endosome disruptor structurally very similar to Compound 1, resulting in selective release of disulfide-tethered doxorubicin into cancer cells. Additionally, the polar quad-Glu polypeptide (SEQ ID NO: 5) or related polar sequences can be used in any of the compounds described herein. Other peptide substrates of MMP-2 (e.g. sequences described in Chen, E. I. et al., *J. Biol. Chem.* 2002, 277, 4485-4491) can also be used in this approach.

Platform/System Design

After receptor-mediated endocytosis, many cell surface receptors and associated membrane lipids traffic through early (primary/sorting) and recycling endosomes (endocytic recycling compartment) before returning to the cell surface, a process termed endocytic recycling. In previous studies of N-alkyl-3β-cholesterylamines, it was reported that appropriately designed derivatives can cycle between the cell surface and intracellular endosomes with recycling kinetics similar to the natural LDL receptor. Based on these results, and reports that the endocytic recycling compartment is a major storage organelle for free (unesterified) cholesterol, an abundant membrane sterol structurally related to N-alkyl-3β-cholesterylamines, it is now conceived that N-alkyl-3β-cholesterylamines, particularly those bearing negative charges in the linker region, selectively accumulate in early/recycling endosomes. The confocal laser scanning microscopy data shown in FIGS. 3A-3B, 7, and 8 of this manuscript confirmed that these compounds become selectively localized in these compartments in CHO cells.

Synthetic Protocols

Chemical reagents and solvents were obtained from Acros, Aldrich and EMD Biosciences. Media and antibiotics were purchased from Mediatech. The CellTiter Glo reagent was from Promega. Commercial grade reagents were used without further purification unless otherwise noted. Anhydrous solvents were obtained after passage through a drying column of a solvent purification system from GlassContour (Laguna Beach, Calif.). All reactions were performed under an atmosphere of dry nitrogen. Reactions were monitored by analytical thin-layer chromatography on plates coated with 0.25 mm silica gel 60 F254 (EMD Chemicals). TLC plates were visualized by UV irradiation (254 nm) or stained with a solution of phosphomolybdic acid in ethanol (20%). Flash column chromatography employed ICN SiliTech Silica Gel (32-63 μm). Purification by preparative reverse phase HPLC employed an Agilent 1100 preparative pump/gradient extension instrument equipped with a Hamilton PRP-1 (polystyrene-divinylbenzene) reverse phase column (7 μm particle size, 21.5 mm×25 cm). The HPLC flow rate was maintained at 25 mL/min for the entire run unless otherwise noted. Melting points were measured with a Thomas Hoover capillary melting point apparatus and were uncorrected. Infrared spectra were obtained with a Perkin Elmer 1600 Series FTIR. NMR spectra were obtained with Bruker CDPX-300, DPX-300, AMX-360, or DRX-400 instruments with chemical shifts reported in parts per million (ppm, δ) referenced to either $CDCl_3$ ($^1H$ 7.27 ppm; $^{13}C$ 77.23 ppm), $MeOH-d_4$ ($^1H$ 4.80 ppm; $^{13}C$ 49.15 ppm), $DMSO-d_6$ ($^1H$ 2.50 ppm; $^{13}C$ 39.51 ppm), or $(CH_3)_4Si$. High-resolution mass spectra were obtained from the Penn State University Mass Spectrometry Facility (ESI and CI). Low-resolution mass spectra were obtained with a Waters ZQ-4000 mass spectrometer. Peaks are reported as m/z.

tert-Butyl-3β-cholest-5-en-3-yl[3-(1,3-dioxo-1,3-dihydro-2H-isoindol-2-yl)propyl]carbamate (Compound 9)

To DMF (10 mL) were added 3β-amino-5-cholestene (Compound 8, 386 mg, 1.0 mmol), N-(3-bromopropyl)phthalimide (295 mg, 1.1 mmol), and $K_2CO_3$ (276 mg, 2.0 mmol). The solution was heated to 60° C. and stirred for 24 h. The reaction was cooled to 22° C., and DMF was removed in vacuo. To the resulting residue was added $CH_2Cl_2$ (10 mL). The insoluble material was removed by filtration and washed with additional $CH_2Cl_2$ (2×5 mL). To the combined filtrate and wash solutions containing the crude secondary amine product was added $(Boc)_2O$ (327 mg, 1.5 mmol) and DIEA (0.5 mL, 3.0 mmol). The reaction was stirred for 4 h at 22° C. and concentrated in vacuo. Flash column chromatography (hexanes/ethyl acetate, 8:1) afforded Compound 9 (465 mg, 69%) as a white foam, mp 59-61° C.; $^1H$ NMR (400 MHz, $CDCl_3$) δ 7.83 (m, 2H), 7.69, (m, 2H), 5.30 (d, 1H), 3.68 (t, 2H), 3.13 (br, 3H), 2.01-0.83 (m, 51H), 0.65 (s, 3H); $^{13}C$ NMR (100 MHz, $CDCl_3$) δ 168.2 (×2), 155.2, 141.3, 133.8 (×2), 132.0 (×2), 123.2 (×2), 79.3, 56.6, 56.1 (×2), 50.1, 42.6 (×2), 39.8, 39.4 (×2), 38.3, 36.8, 36.5, 36.1, 35.9, 35.7, 31.2 (×2), 28.4 (Boc, $Me_3$), 28.2, 27.9, 26.7, 24.2, 23.8 (×2), 22.8, 22.5, 20.9, 19.3, 18.7, 11.8; IR (film) ν max 2935, 2867, 1772, 1715, 1689, 1467, 1395, 1365, 1238, 1172, 1146, 1031, 888, 756, 720 $cm^{-1}$; HRMS (CI+) m/z 673.4946 (M+H+, $C_{43}H_{65}N_2O_4$, requires 673.4944).

tert-Butyl(4R)-5-[(3-{(tert-butoxycarbonyl)-3β-cholest-5-en-3-yl}amino)propyl]amino]-4-{[(9H-fluoren-9-ylmethoxy)carbonyl]amino}-5-oxopentanoate (Compound 10)

To a solution of Compound 9 (202 mg, 0.3 mmol) in absolute ethanol (10 mL) was added anhydrous hydrazine (50 μL, 1.56 mmol). The solution was heated to 50° C. and stirred for 4 h. The reaction was cooled to 22° C., and a white precipitate was removed by filtration. The filtrate was concentrated in vacuo, and the residue was dissolved in $CHCl_3$ (20 mL). After insoluble material was removed by filtration, concentration of the filtrate in vacuo afforded the phthalimide-deprotected primary amine (156 mg, 97%), a white solid that was carried forward without further purification. To N-α-Fmoc-L-glutamic acid, γ-t-butyl ester (130 mg, 0.3 mmol) in anhydrous $CH_2Cl_2$ (10 mL) at 4° C. were added HOBt (40 mg, 0.3 mmol) and EDC (58 mg, 0.3 mmol). This mixture was stirred at 4° C. for 30 min. To this solution was added the phthalimide-deprotected primary amine in anhydrous $CH_2Cl_2$ (5 mL) dropwise. The reaction was allowed to warm to 22° C. and stirred for 12 h. The solution was diluted with $CH_2Cl_2$ (30 mL) and washed with aqueous NaOH (0.1 M, 30 mL) and saturated aqueous NaCl (30 mL). The organic layer was dried over anhydrous $Na_2SO_4$ and concentrated in vacuo. Flash column chromatography (hexanes/ethyl acetate, 2:1) afforded 10 (203 mg, 91%) as a white solid, mp 83-85° C.; $^1H$ NMR (300 MHz, $CDCl_3$) δ 7.74 (d, J=7.5 Hz, 2H), 7.63 (d, J=7.5 Hz, 2H), 7.38 (t, J=7.5 Hz, 2H), 7.29 (t, J=7.5 Hz, 2H), 5.88 (d, 1H), 5.31 (d, 1H), 4.37 (d, J=7.1 Hz, 2H), 4.16 (br, 1H), 4.15 (t, J=7.1 Hz, 1H), 3.27 (m, 4H), 2.60-0.85 (m, 65H), 0.66 (s, 3H); $^{13}C$ NMR (75 MHz, $CDCl_3$) δ 172.6, 171.0, 156.3, 143.9, 143.8, 141.2 (×3), 127.6 (×2), 125.2 (×2), 121.4, 119.9 (×2), 80.7, 79.8, 67.0, 58.2, 56.7, 56.1 (×2), 54.5, 50.1, 47.1, 42.3, 41.3, 39.7, 39.5, 38.4, 37.1, 36.7, 36.2, 35.8, 31.9 (×2), 31.7, 28.5 (Boc, $Me_3$), 28.4, 28.2, 28.1 (×4), 28.0, 26.8, 24.3, 23.8, 22.8, 22.6, 21.0, 19.4, 18.7, 11.8; IR (film) ν max 3310, 2935, 2868, 1728, 1668, 1531, 1450, 1412, 1366, 1249, 1163, 1048, 757 $cm^{-1}$; HRMS (ESI+) 950.6640 m/z (M+H+, $C_{59}H_{88}N_3O_7$ requires 950.6622).

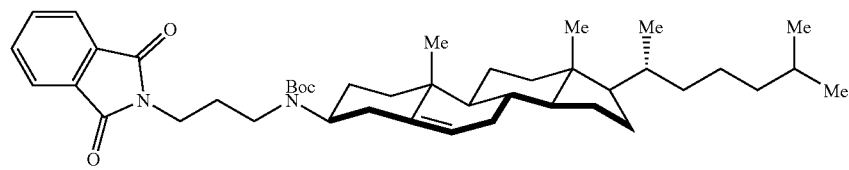

9

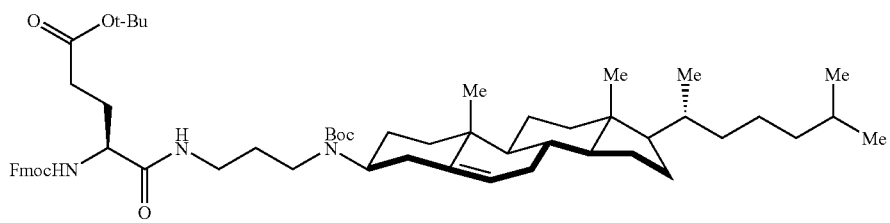

tert-Butyl(11S,14S)-11-(3-tert-butoxy-3-oxopropyl)-
5-(3β-cholest-5-en-3-yl)-14-{[(9H-fluoren-9-yl-
methoxy)carbonyl]amino}-2,2-dimethyl-4,10,13-
trioxo-3-oxa-5,9,12-triazaheptadecan-17-oate
(Compound 11)

Compound 10 (160 mg, 0.17 mmol) was dissolved in DMF (2 mL) containing piperidine (20%) and stirred for 30 min at 22° C. The solvent was removed in vacuo, and the primary amine derived from 10 was dissolved in anhydrous $CH_2Cl_2$ (5 mL). To a solution of N-α-Fmoc-L-glutamic acid, γ-t-butyl ester (80 mg, 0.19 mmol) in anhydrous $CH_2Cl_2$ (10 mL) at 4° C. were added HOBt (27 mg, 0.2 mmol) and EDC (40 mg, 0.2 mmol) and the solution was stirred for 30 min. The solution of crude primary amine derived from 10 was added. The reaction was allowed to warm to 22° C. and was stirred for 12 h. This solution was diluted with $CH_2Cl_2$ (30 mL) and washed with aqueous NaOH (0.1 M, 30 mL) and saturated aqueous NaCl (30 mL). The organic layer was dried over anhydrous $Na_2SO_4$ and concentrated in vacuo. Flash column chromatography (hexanes/ethyl acetate, 2:1) afforded 11 (172 mg, 89%) as a white solid, mp 90-92° C.; $^1H$ NMR (400 MHz, $CDCl_3$) δ 7.75 (d, J=7.5 Hz, 2H), 7.60 (d, J=7.5 Hz, 2H), 7.38 (t, J=7.5 Hz, 2H), 7.30 (t, J=7.5 Hz, 2H), 5.90 (br, 1H), 5.29 (d, 1H), 4.41 (br, 1H) 4.36 (d, J=7.1 Hz, 2H), 4.20 (t, J=7.1 Hz, 1H), 3.60 (br, 1H), 3.24 (br, 4H), 2.60-0.86 (m, 76H), 0.67 (s, 3H); $^{13}C$ NMR (100 MHz, $CDCl_3$) δ 172.9, 172.2, 171.3, 170.6, 156.4, 156.2, 143.9, 143.7, 141.3 (×3), 127.7 (×2), 127.1 (×2), 125.1 (×2), 121.3, 119.9 (×2), 81.0, 80.5, 79.3, 67.1, 56.7, 56.1 (×2), 53.0, 50.1 (×2), 47.2, 47.1, 46.5, 42.3 (×2), 39.7, 39.5 (×2), 38.4, 36.7, 36.2, 35.8, 31.9 (×2), 31.7, 28.5 (Boc, $Me_3$), 28.3, 28.2, 28.1, 28.0 (×10), 26.8, 24.2, 23.8, 22.8 (×2), 22.6 (×2), 21.0, 19.4, 19.1, 18.7, 11.8; IR (film) ν max 3306, 2934, 2868, 1727, 1650, 1531, 1450, 1412, 1392, 1367, 1249, 1156, 1049, 960, 848, 757 $cm^{-1}$; HRMS (ESI+) 1135.7745 m/z ($M+H^+$, $C_{68}H_{103}N_4O_{10}$ requires 1135.7674).

3-[(2-{[(9H-Fluoren-9-ylmethoxy)carbonyl]
amino}ethyl)dithio]propanoic acid (Compound 12)

To a solution of 3-(2-aminoethyldithio)propanoic acid (500 mg, 2.8 mmol) and $NaHCO_3$ (700 mg, 8.3 mmol) in $H_2O$ (50 mL) was added a solution of 9-fluorenylmethyl chloroformate (870 mg, 3.3 mmol) in dioxane (25 mL). The reaction was stirred for 16 h at 22° C. The solution was washed with diethyl ether (2×50 mL) and adjusted to pH=1.0 with aqueous HCl (2.0 M). The aqueous phase was extracted with EtOAc (2×50 mL). The combined organic extracts were washed with saturated aqueous NaCl (30 mL), dried over anhydrous $Na_2SO_4$, and concentrated in vacuo. Flash column chromatography ($CH_2Cl_2/CH_3OH$, 30:1) afforded 12 (766 mg, 68%) as a white solid, mp 104-106° C.; $^1H$ NMR (300 MHz, $CDCl_3$) δ 8.69 (br, 1H), 7.75 (d, J=7.5 Hz, 2H), 7.60 (d, J=7.5 Hz, 2H), 7.38 (t, J=7.5 Hz, 2H), 7.30 (t, J=7.5 Hz, 2H), 5.25 (br, 1H), 4.39 (d, J=7.1 Hz, 2H), 4.20 (t, J=7.1 Hz, 1H), 3.50 (m, 2H), 2.90 (t, 2H), 2.76 (m, 4H); $^{13}C$ NMR (75 MHz, $CDCl_3$) δ 176.7, 156.5, 143.8 (×2), 141.3 (×2), 127.7 (×2), 127.1 (×2), 125.0 (×2), 120.0 (×2), 66.8, 47.2, 39.7, 37.9, 33.9, 32.9; IR (film) ν max 3600-2500 (br), 3331, 3045, 2954, 2915, 1697, 1544, 1442, 1412, 1279, 1146, 1021, 987, 938, 739, 648 $cm^{-1}$; LRMS (ESI+) 426.0 m/z ($M+Na^+$, $C_{20}H_{21}NO_4S_2Na$ requires 426.1).

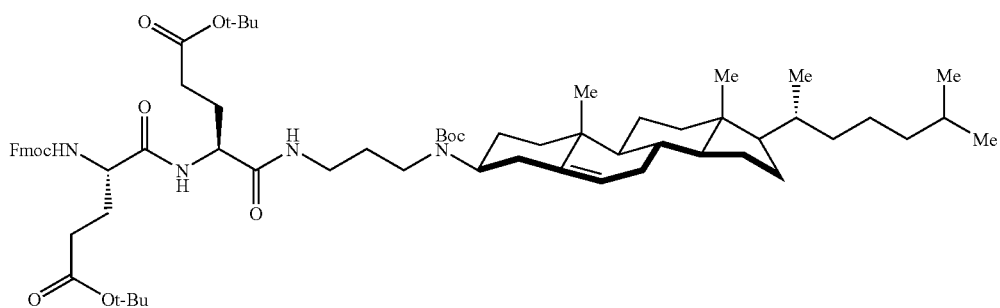

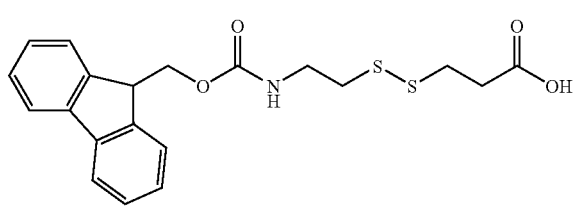

12 tert-Butyl(13S,16S)-16-{[(3-{(tert-butoxycarbonyl)(3β-cholest-5-en-3-yl)amino}propyl)amino]carbonyl}-13-(3-tert-butoxy-3-oxopropyl)-1-(9H-fluoren-9-yl)-3,11,14-trioxo-2-oxa-7,8-dithia-4,12,15-triazanonadecan-19-oate (Compound 14)

Compound 11 (100 mg, 0.088 mmol) was dissolved in DMF (2 mL) containing piperidine (20%) and stirred for 30 min at 22° C. The solvent was removed in vacuo, and the primary amine derived from 11 was dissolved in anhydrous CH$_2$Cl$_2$ (5 mL). To a solution of 3-[(2-{[(9H-fluoren-9-ylmethoxy)carbonyl]amino}ethyl)dithio]propanoic acid (12) (40 mg, 0.1 mmol) in anhydrous CH$_2$Cl$_2$ (5 mL) at 4° C. were added HOBt (15 mg, 0.11 mmol) and EDC (21 mg, 0.11 mmol) and the solution was stirred for 30 min. The solution of primary amine derived from 11 was added. The reaction was allowed to warm to 22° C. and was stirred for 12 h. This solution was diluted with CH$_2$Cl$_2$ (20 mL) and washed with aqueous NaOH (0.1 M, 20 mL) and saturated aqueous NaCl (20 mL). The organic layer was dried over anhydrous Na$_2$SO$_4$ and concentrated in vacuo. Flash column chromatography (hexanes/ethyl acetate, 1:1) afforded 14 (92 mg, 81%) as a glassy solid; $^1$H NMR (400 MHz, CDCl$_3$) δ 7.75 (d, J=7.5 Hz, 2H), 7.60 (d, J=7.5 Hz, 2H), 7.39 (t, J=7.5 Hz, 2H), 7.30 (t, J=7.5 Hz, 2H), 5.31 (d, 1H), 4.50 (br, 2H), 4.39 ((d, J=7.1 Hz, 2H), 4.22 (t, J=7.1 Hz, 1H), 3.50 (br, 2H), 3.30 (br, 1H), 3.22 (br, 4H), 2.98 (t, 2H), 2.81 (t, 2H), 2.66-0.86 (m, 79H), 0.67 (s, 3H); $^{13}$C NMR (100 MHz, CDCl$_3$) δ 173.2, 172.7, 171.3, 171.1, 170.7, 156.5, 156.1, 143.9 (×2), 141.3 (×3), 127.7 (×2), 127.0 (×2), 125.1 (×2), 121.3, 120.0 (×2), 81.1, 80.8, 79.8, 66.7, 58.3, 56.7, 56.1 (×2), 52.8 (×2), 50.1, 47.2, 42.3, 41.7, 39.8, 39.7, 39.5, 38.4, 38.0, 37.2, 36.7, 36.2, 35.8, 33.9, 31.9 (×3), 29.7, 28.5 (Boc, Me$_3$), 28.3, 28.2, 28.1 (×6), 28.0, 27.7, 26.8, 24.3, 23.8, 22.8, 22.6, 21.0, 19.5, 18.7, 11.9; IR (film) ν max 3292, 2934, 2868, 1729, 1683, 1635, 1538, 1450, 1411, 1366, 1253, 1156, 903, 848, 780, 757 cm$^{-1}$; HRMS (ESI+) 1298.7854 m/z (M+H$^+$, C$_{73}$H$_{112}$N$_5$O$_{11}$S$_2$ requires 1298.7800).

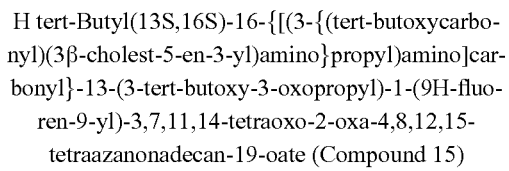

5

H tert-Butyl(13S,16S)-16-{[(3-{(tert-butoxycarbonyl)(3β-cholest-5-en-3-yl)amino}propyl)amino]carbonyl}-13-(3-tert-butoxy-3-oxopropyl)-1-(9H-fluoren-9-yl)-3,7,11,14-tetraoxo-2-oxa-4,8,12,15-tetraazanonadecan-19-oate (Compound 15)

Compound 11 (80 mg, 0.070 mmol) was dissolved in DMF (2 mL) containing piperidine (20%) and stirred for 20 min at 22° C. The solvents were removed in vacuo, and the primary amine derived from 11 was dissolved in anhydrous CH$_2$Cl$_2$ (5 mL). To a solution of 3-[(3-{[(9H-fluoren-9-ylmethoxy)carbonyl]amino}propanoyl)amino]propanoic acid (13)$^6$ (30 mg, 0.077 mmol) in anhydrous CH$_2$Cl$_2$ (5 mL) at 4° C. were added HOBt (11 mg, 0.077 mmol) and EDC (15 mg, 0.077 mmol). The solution was stirred for 30 min at 4° C. The solution of the crude primary amine derived from 11 was added and the reaction was allowed to warm to 22° C. and was stirred for 12 h. This solution was diluted with CH$_2$Cl$_2$ (20 mL), washed with aqueous NaOH (0.1 M, 20 mL), and washed with saturated aqueous NaCl (20 mL). The organic layer was dried over anhydrous Na$_2$SO$_4$ and concentrated in vacuo. Flash column chromatography (hexanes/ethyl acetate, 1:1) afforded 15 (75 mg, 89%) as a white solid, mp 136-137° C.; $^1$H NMR (400 MHz, CDCl$_3$) δ 7.76 (d, J=7.5 Hz, 2H), 7.61 (d, J=7.4 Hz, 2H), 7.39 (t, J=7.4 Hz, 2H), 7.31 (t, J=7.4 Hz, 2H), 5.32 (d, J=5.8 Hz, 1H), 4.40 (br, 2H), 4.34 (d, J=7.0 Hz, 2H), 4.20 (t, J=7.0 Hz, 1H), 3.61 (br, 2H), 3.52-3.30 (m, 5H), 3.2 (br, 2H), 2.66-0.86 (m, 81H), 0.68 (s, 3H); $^{13}$C NMR (100 MHz, CDCl$_3$) δ 173.0 (×2), 172.8, 172.5, 172.1, 170.0, 157.0, 156.8, 144.0 (×3), 141.4 (×2), 127.7 (×2), 127.0 (×2), 125.1 (×2), 121.3, 120.0 (×2), 81.1, 80.8, 79.8, 66.9, 66.8, 56.8, 56.2, 53.5, 52.6, 50.2, 47.3 (×2), 46.7, 43.0, 42.4, 39.8, 39.6, 38.5, 37.4, 37.2, 36.8, 36.3, 36.1, 35.9, 33.2, 32.9, 32.0, 31.9, 31.7, 28.5 (×3, Boc, Me$_3$), 28.3, 28.1, 28.0 (×6), 27.8, 26.9, 26.4, 25.6, 24.4, 23.9, 22.9, 22.6, 21.1, 19.4, 18.7, 11.9; IR (film) ν max 3290, 3068, 2935, 2868, 1727, 1688, 1634, 1538, 1449, 1416, 1367, 1253, 1157, 1026, 960, 903, 850, 757, 666 cm$^{-1}$; HRMS (ESI+) 1277.8502 m/z (M+H$^+$, C$_{74}$H$_{113}$N$_6$O$_{12}$ requires 1277.8416).

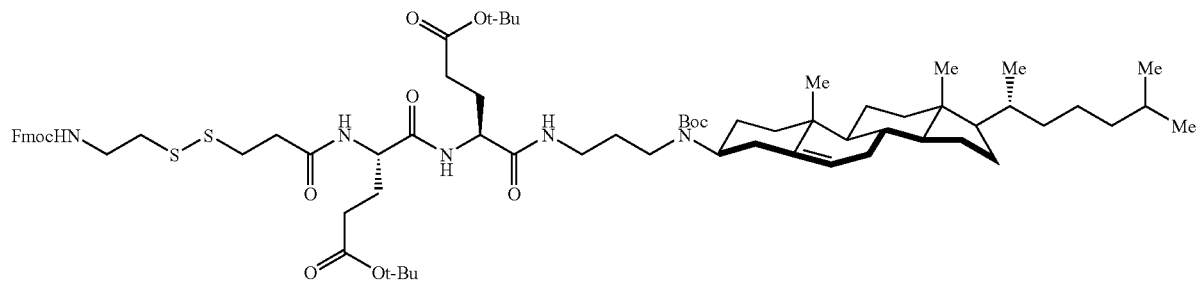

14

15

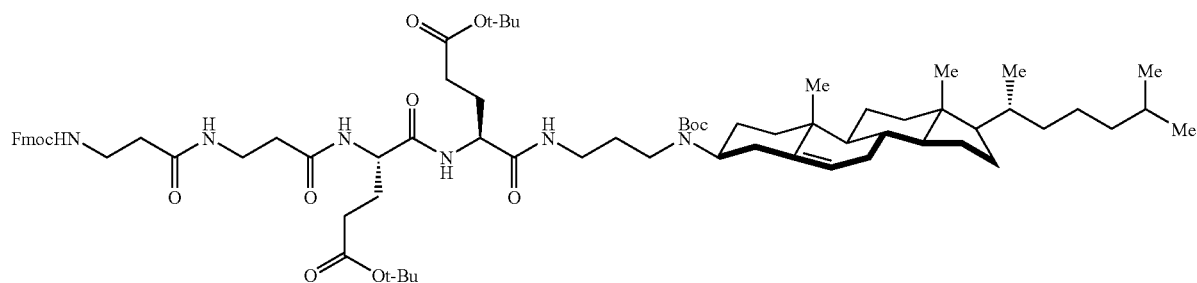

(11S,14S)-11-(2-Carboxylatoethyl)-1-[3-carboxy-lato-4-(6-oxido-3-oxo-3H-xanthen-9-yl)phenyl]-14-[({3-(3β-cholest-5-en-3-ylammonio)propyl}amino)carbonyl]-1,9,12-trioxo-5,6-dithia-2,10,13-triazaheptadecan-17-oate (Compound 3)

Compound 14 (29 mg, 0.022 mmol) was dissolved in DMF (2 mL) containing piperidine (20%) and stirred for 30 min at 22° C. The solvent was removed in vacuo, and the primary amine derived from 14 was dissolved in anhydrous DMF (5 mL). To this solution was added 5-carboxyfluorescein, succinimidyl ester (20 mg, 0.045 mmol) and DIEA (170 μL, 0.1 mmol). The reaction was stirred for 12 h at 22° C. followed by concentration in vacuo. The residue was dissolved in $CH_2Cl_2$ (10 mL) containing TFA (20%) and stirred for 12 h at 22° C. The reaction was concentrated in vacuo, and the crude product was purified by preparative reverse-phase HPLC (gradient: 9.95% MeCN, 89.95% $H_2O$, and 0.1% TFA to 99.9% MeCN, 0% $H_2O$, and 0.1% TFA over 25 min; retention time=18.5 min (215 nm)), which afforded 3 (23 mg, 85%) as a yellow solid, mp 194-197° C.; $^1$H NMR (400 MHz, MeOH-$d_4$) δ 8.52-7.68 (m, 3H), 7.38 (d, 1H), 6.75-6.58 (m, 6H), 5.42 (s, 1H), 4.35-4.25 (m, 2H), 3.78 (t, 1H), 3.35 (t, 1H), 3.08-2.89 (m, 7H), 2.80-2.67 (m, 2H), 2.48-2.37 (m, 6H), 2.20-0.89 (m, 46H), 0.72 (s, 3H); $^{13}$C NMR (100 MHz, MeOH-$d_4$) δ 176.5, 176.4, 176.3, 174.7, 174.6, 174.3 (×2), 170.4, 168.3, 168.2, 162.0, 154.4 (×2), 142.0, 139.4, 137.6, 135.4, 130.5, 130.4 (×2), 128.9, 126.0, 125.3, 124.8, 114.2 (×2), 111.0, 103.7, 59.4, 58.0, 57.5, 55.1, 55.0, 54.9, 51.3, 43.4 (×2), 43.2, 41.0, 40.7 (×2), 40.6, 38.5, 38.1, 37.8, 37.3, 37.1, 36.9, 36.4, 35.4, 33.0, 32.9, 31.2, 29.3, 29.1, 27.7, 27.6, 26.2, 25.3, 24.9, 23.2, 22.9, 22.0, 19.6, 19.2, 12.3; IR (film) v max 3700-2500 (br), 3301, 3068, 2940, 2847, 1725, 1707, 1661, 1644, 1550, 1538, 1498, 1453, 1311, 1247, 1195, 1180, 1136, 1113, 846, 793, 756, 718 cm$^{-1}$; HRMS (ESI+) m/z 1222.5847 (M+H$^+$, $C_{66}H_{88}N_5O_{13}S_2$ requires 1222.5820).

3

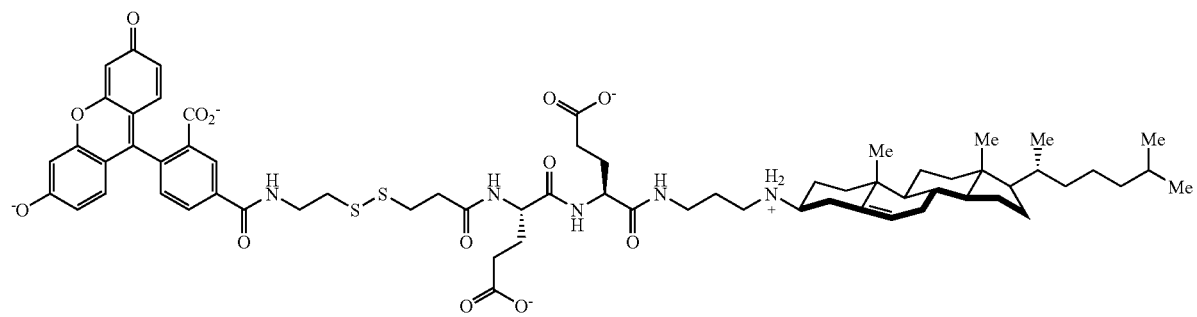

(11S,14S)-11-(2-Carboxylatoethyl)-1-[3-carboxy-lato-4-(6-oxido-3-oxo-3H-xanthen-9-yl)phenyl]-14-[({3-(3β-cholest-5-en-3-ylammonio)propyl}amino)carbonyl]-1,5,9,12-tetraoxo-2,6,10,13-tetraazaheptadecan-17-oate (Compound 4)

Compound 15 (41 mg, 0.032 mmol) was dissolved in DMF (2 mL) containing piperidine (20%) and stirred for 30 min at 22° C. The solvent was removed in vacuo, and the primary amine derived from 15 was dissolved in anhydrous $CH_2Cl_2$ (5 mL). To this solution was added 5-carboxyfluorescein, succinimidyl ester (26 mg, 0.06 mmol) and DIEA (170 μL, 0.1 mmol). The reaction was stirred for 12 h at 22° C. followed by concentration in vacuo. The residue was dissolved in $CH_2Cl_2$ (10 mL) containing TFA (20%) and stirred for 12 h at 22° C. The reaction was concentrated in vacuo, and the crude product was purified by preparative reverse-phase HPLC (gradient: 9.9% MeCN, 90% $H_2O$, and 0.1% TFA to 99.9% MeCN, 0% $H_2O$, and 0.1% TFA over 25 min; retention time=17.6 min (215 nm)) to afford 4 (37 mg, 88%) as a yellow solid, mp 202-205° C.; $^1$H NMR (300 MHz, MeOH-$d_4$) δ 8.47-7.64 (m, 3H), 7.38 (d, 1H), 6.74-6.54 (m, 6H), 5.45 (s, 1H), 4.31-4.23 (m, 2H), 3.72 (t, 1H), 3.63-3.40 (m, 3H), 3.34 (t, 1H), 3.14 (t, 3H), 3.05 (m, 2H), 2.93 (m, 1H), 2.58-2.34 (m, 6H), 2.11-0.85

(m, 46H), 0.72 (s, 3H); $^{13}$C NMR (100 MHz, DMSO-$d_6$) δ 174.0(×2), 173.9(×2), 171.4(×2), 171.0, 170.4, 168.2, 159.8, 158.4, 158.1, 151.8, 149.8, 140.7, 138.8, 134.6, 129.0, 124.2, 123.4, 123.0, 122.2, 120.8, 117.9, 115.0, 112.7, 112.1, 109.0, 102.3, 56.4, 56.1, 55.6, 52.3, 52.1, 49.1, 47.4, 43.5 (×2), 41.8, 41.0, 36.4, 36.2, 35.7, 35.3, 35.2, 33.3 (×2), 31.3, 30.6, 30.5 (×2), 27.4, 27.0, 25.9, 25.5, 25.4, 24.5, 24.2, 23.2, 22.7, 22.4, 22.1 (×2), 21.7, 18.8, 18.6, 11.7; IR (film) ν max 3700-2500 (br), 3266, 3068, 2930, 2847, 1713, 1667, 1632, 1591, 1537, 1453, 1384, 1307, 1274, 1245, 1200, 1177, 1133, 920, 845, 799 cm$^{-1}$; HRMS (ESI+) 1201.6511 m/z (M+H$^+$, $C_{67}H_{89}N_6O_{14}$ requires 1201.6437).

resin by addition of DMF solution (2 mL) of amino acid (4.0 eq.), HOBt (3.8 eq.), HBTU (3.8 eq.) and DIEA (8.0 eq.) with shaking at 22° C. for 2 h. Deprotection of Fmoc carbamates on the resin was carried out by addition of piperidine (20%) in DMF (2 mL for 5 min followed by 2 mL for 15 min and 2 mL for 5 min (×2)). After removal of the final Nα-Fmoc group of the N-terminal amino acid of 5, the free amine was capped by shaking the resin for 5 min with acetic anhydride (0.5 M) and 2,6-lutidine (0.5 M) in DMF (2 mL). The capped resin was subsequently washed with DMF (5×2 mL). The peptide was

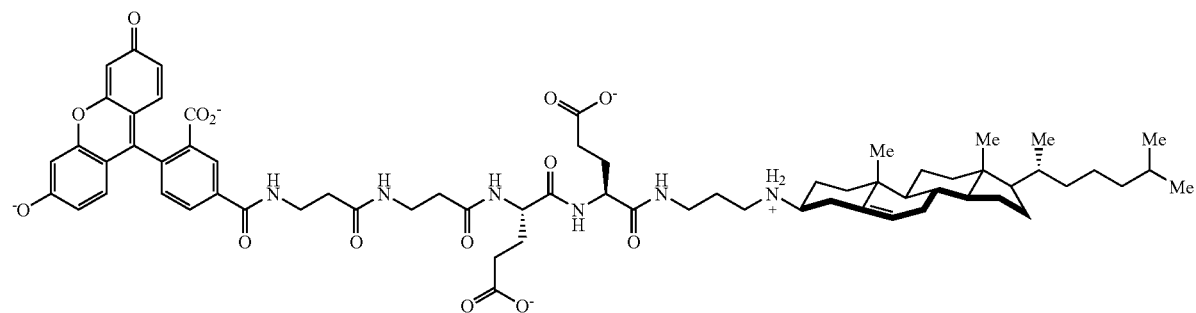

4

N-Acetyl-L-seryl-L-seryl-L-alanyl-L-tryptophyl-L-tryptophyl-L-seryl-L-tyrosyl-L-tryptophyl-L-prolyl-L-prolyl-L-valyl-L-alaninamide (Compound 5) (SEQ ID NO: 1)

Peptide synthesis employed a Burrell Wrist-Action Laboratory Shaker and standard N-Fmoc methodology. The peptide was constructed with Rink amide Novagel resin (0.62 mmol/g, 50 mg, 0.032 mmol) using the following Fmoc protected amino acids: Fmoc-Ala-OH, Fmoc-Val-OH, Fmoc-Pro-OH, Fmoc-Trp-OH, Fmoc-Tyr(t-Bu)-OH, Fmoc-Ser(t-Bu)-OH, Fmoc-Glu(t-Bu)-OH, Fmoc-Lys(Boc)-OH, Fmoc-β-Ala-OH. Amino acids were consecutively coupled to the cleaved from the resin with concurrent removal of t-Bu side chain protecting groups by treatment with TFA/TIPS/H$_2$O (90:8:2) with shaking for 2 h. The resin was removed by filtration and washed with CH$_2$Cl$_2$ (3×1 mL). The filtrates were combined and concentrated in vacuo. The crude product was dissolved in MeOH (1 mL) and purified by preparative reverse-phase HPLC (gradient: 90% H$_2$O, 9.9% MeCN, and 0.1% TFA to 99.9% MeCN and 0.1% TFA over 20 min; retention time=10.8 min (254 nm) to afford 5 as an off-white solid (8.3 mg, 18.0%). LRMS (ESI+) m/z 1478.0 (M+H$^+$, $C_{74}H_{93}N_{16}O_{17}$ requires 1478.6).

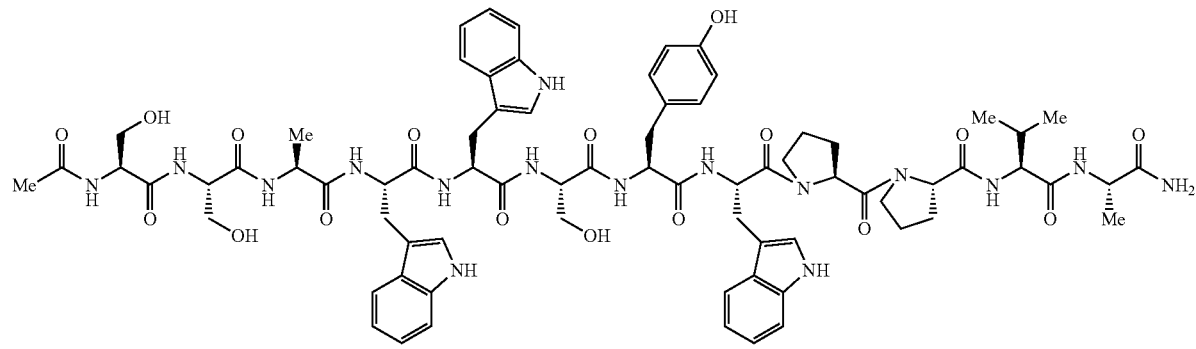

5

N-[6-({6-[(N-{5-(3β-Cholest-5-en-3-ylammonio) pentanoyl}-5-oxidanidyl-5-oxidanylidene-L-norvalyl-5-oxidanidyl-5-oxidanylidene-L-norvalyl)amino] hexanoyl}amino)hexanoyl]-L-seryl-L-seryl-L-alanyl-L-tryptophyl-L-tryptophyl-L-seryl-L-tyrosyl-L-tryptophyl-L-prolyl-L-prolyl-L-valyl-L-alaninamide (Compound 1 having SEQ ID NO: 1).

The side-chain protected peptide sequence (EE-ε-Ahx-ε-Ahx-SSAWWSYWPPVA) (SEQ ID NO: 6) was constructed on Rink amide Novagel resin (0.62 mmol/g, 120 mg, 0.076 mmol) using the method described for preparation of peptide 5. After removal of the Nα-Fmoc group of the N-terminal amino acid, the free amine was acylated by addition of 5-{(tert-butoxycarbonyl)[(3β)-cholest-5-en-3-yl]amino}pentanoic acid and the amino acid coupling reagents used to prepare 5. The product was cleaved from the resin with TFA/TIPS/H$_2$O (90:8:2) by shaking for 2 h and purified by preparative reverse phase-HPLC (gradient: 90% H$_2$O, 9.9% MeCN, and 0.1% TFA to 99.9% MeCN and 0.1% TFA over 20 min; retention time=16.7 min (254 nm)) to afford 1 as a white solid (27 mg, 15.0%). LRMS (ESI+) m/z 2389.1 (M+H$^+$, C$_{126}$H$_{180}$N$_{21}$O$_{25}$ requires 2388.9).

N-(6-{[6-({N-{5-(3β-Cholest-5-en-3-ylammonio) pentanoyl}-5-oxidanidyl-5-oxidanylidene-L-norvalyl-N$^6$-[4-carboxy-2,5-dichloro-3-(2,4,5,7-tetrachloro-6-hydroxy-3-oxo-3H-xanthen-9-yl)benzoyl]-L-lysyl}amino)hexanoyl]amino}hexanoyl)-L-seryl-L-seryl-L-alanyl-L-tryptophyl-L-tryptophyl-L-seryl-L-tyrosyl-L-tryptophyl-L-prolyl-L-prolyl-L-valyl-L-alaninamide (Compound 2 having SEQ ID NO: 1)

The side-chain protected peptide sequence (EK-ε-Ahx-ε-Ahx-SSAWWSYWPPVA (SEQ ID NO: 6)) was constructed on Rink amide Novagel resin (0.62 mmol/g, 60 mg, 0.038 mmol) using the method described for preparation of Compound 1. After removal of the Nα-Fmoc group of the N-terminal amino acid, the free amine was acylated by coupling with 5-{(tert-butoxycarbonyl) [(3β)-cholest-5-en-3-yl] amino}pentanoic acid as described for the preparation of Compound 1. The product was cleaved from resin with TFA/TIPS/H$_2$O (90:8:2) by shaking for 2 h and purified by preparative reverse-phase HPLC (gradient: 90% H$_2$O, 9.9% MeCN, and 0.1% TFA to 99.9% MeCN and 0.1% TFA over 30 min; retention time 18.4 min (254 nm)) to afford a white solid (12 mg, 13.6%), the fully deprotected intermediate bearing an unmodified Lys residue. This material was dissolved in DMSO (2 mL) and treated with 6-carboxy-2',4,4',5',7,7'-hexachlorofluorescein, succinimidyl ester (5 mg, 1.5 eq.) and DIEA (9 mL, 10 eq.). The reaction was stirred overnight at 22° C., concentrated in vacuo, and the crude product was

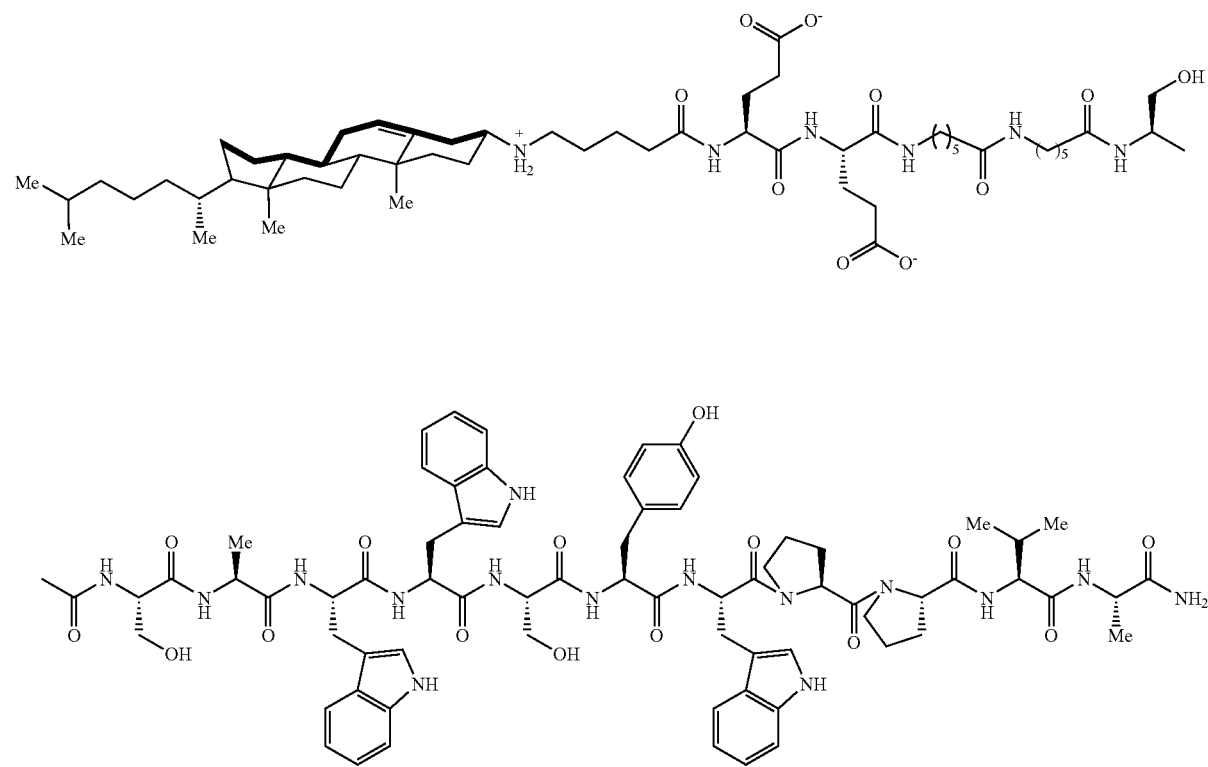

purified by preparative reverse-phase HPLC (gradient: 90% H$_2$O, 9.9% MeCN, and 0.1% TFA to 99.9% MeCN and 0.1% TFA over 20 min; retention time=18.5 min (254 nm)) to afford 2 as a purple solid (7.2 mg, 6.6%). LRMS (ESI+) m/z 2952.3 (M+H$^+$, C$_{148}$H$_{189}$C$_{16}$N$_{22}$O$_{29}$ requires 2952.9)

alcohol, alkoxy, halogen, haloalkyl, hydroxy, amine, carboxyl, amide, combinations thereof, or the like. Derivatives, are considered to include atom or substituent exchanges such as one or more hydrogen atoms being substituted with an alkyl, halogen, hydroxy, amine, combinations thereof, or the

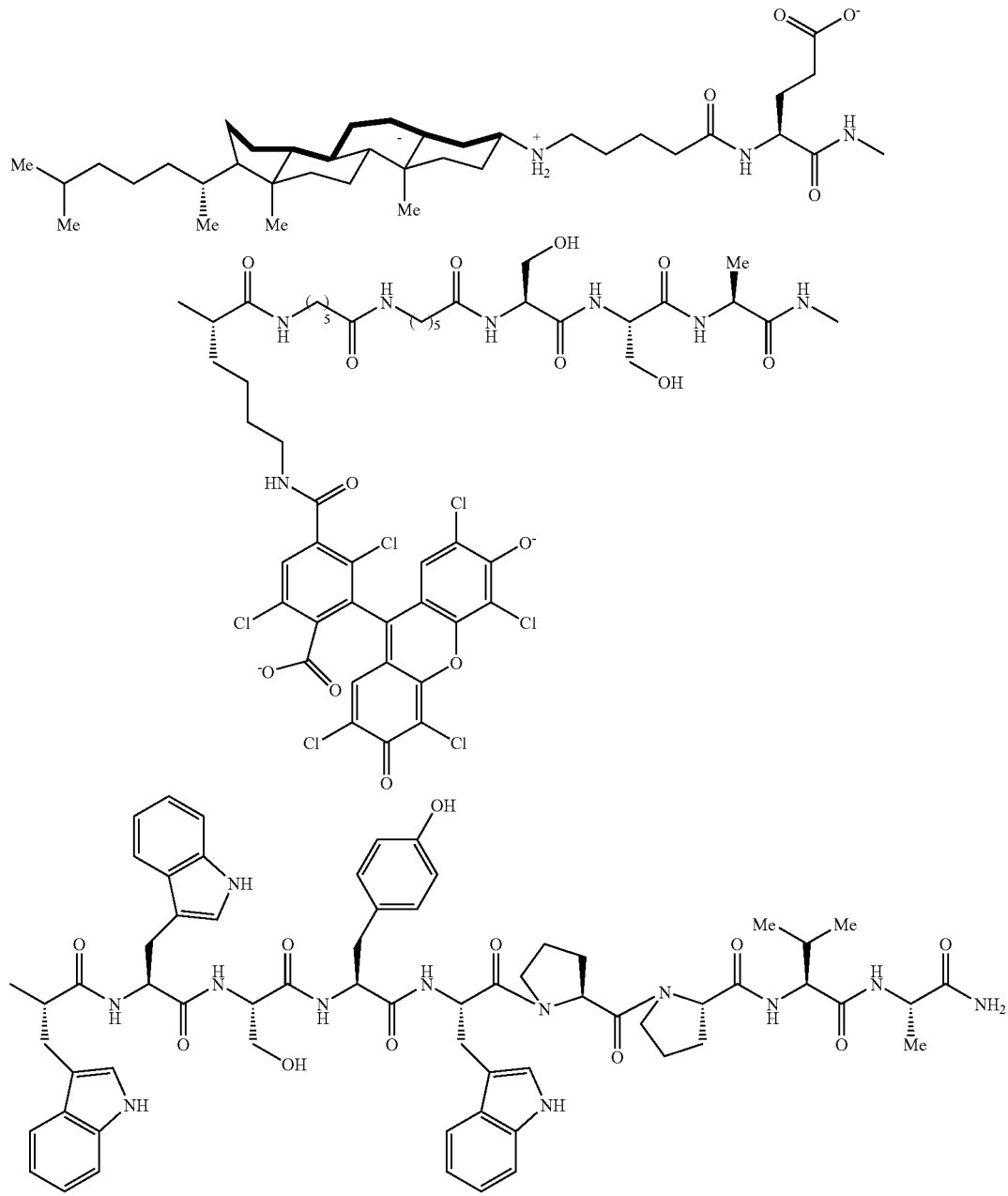

2

From the foregoing chemical synthetic processes as well as chemistry generally known to those of skill in the art, the embodiments of the present invention can be prepared. This includes embodiments with a branched linker or analogs and derivatives of the compounds. As used herein, "analogs" are considered to include group substitutions of selected functional groups or moieties of the linker with different functional groups or moieties. Examples of analogs include moieties being substituted with like moieties, with a alkyl, aryl, like. Analogs constitute major substituent exchanges, whereas derivatives constitute minor substituent exchanges with hydrogens or other single atoms.

The term "alkoxy" embraces oxy-containing groups substituted with an alkyl group. Examples include, without limitation, methoxy, ethoxy, and tert-butoxy. Most preferred are "lower alkoxy" groups having one to six carbon atoms. Examples of such groups include methoxy, ethoxy, propoxy, butoxy, isopropoxy, and tert-butoxy.

As used herein, the term "alcohol" embraces an alkyl group having one or more hydroxy (—OH) substituents. Primary, secondary, and tertiary alcohols are contemplated, such as mono-alcohols as well as polyhydroxy variants. Preferred alcohols are those containing from about one up to six carbon atoms. Exemplary of preferred aliphatic alcohols are: methanol, ethanol, 1-propanol, 2-propanol, 1-propen-2-ol, 1-butanol, 2-butanol, 2-methyl-2-propanol, 1-pentanol, 2-pentanol, 3-pentanol, and 3-methyl-1-butanol.

As used herein, the term "halo" or "halogen" embraces to fluoro, chloro, bromo, or iodo, usually regarding halo substitution for a hydrogen atom in an organic compound. Of the halogens, fluorine is the most preferred.

As used herein, the term "haloalkyl" refers to an alkyl group having at least one halogen thereon. The term includes monohaloalkyl, dihaloalkyl, and trihaloalkyl groups. Examples of haloalkyl groups include fluoromethyl, difluoromethy, trifluoromethyl, fluoroethyl, pentafluoroethyl, 2,2,2-trifluoroethyl, and 2,2,3,3,3-pentafluoropropyl.

Biological Protocols
Cell Culture

Jurkat lymphocytes (human acute leukemia, ATCC #TIB-152) were cultivated in Roswell Park Memorial Institute (RPMI) 1640 medium supplemented with Fetal Bovine Serum (FBS, 10%), penicillin (100 units/mL), and streptomycin (100 μg/mL). CHO-K1 cells (Chinese hamster ovary cells, ATCC #CCL-61) were cultivated in F-12K medium supplemented with Fetal Bovine Serum (FBS, 10%), penicillin (100 units/mL), and streptomycin (100 μg/mL). Both cell lines were propagated in a humidified 5% $CO_2$ incubator at 37° C. Media used for cell culture and wash steps contained antibiotics and FBS unless otherwise noted.

Microscopy

A Zeiss LSM 5 Pascal confocal laser-scanning microscope fitted with a Plan Apochromat objective (63×) was employed. Fluorescein and Alexa Fluor-488 were excited with a 488 nm Argon ion laser (25 mW, 1% laser power) and emitted photons were collected through 505 nm LP filter. Excitation of 6-Hex, Texas Red, and DiI employed a 543 nm HeNe laser and emitted photons were collected through a 560 nm LP filter.

Flow Cytometry

Analyses were performed with a Beckman-Coulter XL-MCL bench-top flow cytometer. Forward-scatter (FS) and side-scatter (SSC) dot plots afforded cellular physical properties of size and granularity that allowed gating of live cells. After gating, 10,000 cells were counted. In studies of endosomal release of fluorescein derivative Compound 6 mediated by Compound 1, the fluorophore was excited at 488 nm with a 15 mW air-cooled argon-ion laser, the emission was split with a 550 nm dichroic and filtered through a 510 nm long pass filter and 530/30-nm band pass filter using the XL-MCL cytometer. The PMT voltage for this instrument was set to 501 for Jurkat cells and 524 for CHO cells.

Examination of Colocalization of Red Fluorescent and Green Fluorescent Compounds and Proteins by Confocal Microscopy CHO cells ($1.2 \times 10^5$) in media (2 mL) were cultivated on round collagen-coated coverslips (22 mm, BD BioCoat) in a 6-well plate. After incubation at 37° C. for 24 h, media was discarded and replaced with fresh media (2 mL). Cells were treated with 2 (final concentration=2 μM) and/or Compound 3 (final concentration=5 μM) in DMSO (final [DMSO]=1%) at 37° C. for 12 h followed by washing with fresh media (2 mL). Cells treated with Compound 2 and Compound 3 were immediately analyzed by confocal microscopy after the wash step. Cells treated with Compound 3 alone were incubated with media containing transferrin, Texas Red conjugate (Invitrogen, final concentration 500 nM) or DiI-LDL (Biomedical Technologies Inc., final concentration 8 nM). Cells treated with Compound 2 were incubated with media containing transferrin, Alexa Fluor 488 conjugate (Invitrogen, final concentration=610 nM). Cells treated with these fluorescent protein markers of early/recycling or late endosomal/lysosomal compartments were incubated at 37° C. for 5 min, washed with fresh media (2 mL), and analyzed by confocal microscopy.

Cytotoxicity Assays
Jurkat Cells

Jurkat lymphocytes ($7 \times 10^4$) in media (100 μL) were loaded on a 96-well plate. To these cells were added increasing concentrations of Compound 1 in DMSO (final [DMSO]=1%). After incubation for 48 h, cells from each well (10 μL) were transferred to an opaque 96-well plate containing PBS (170 μL per well) and treated with CellTiter-Glo reagent (20 μL, Promega) according to the Promega protocol provided with the reagent. After incubation at ambient temperature (22° C.) for 10 min, the luminescence of the samples was measured with a Packard Fusion microplate reader.

CHO Cells

Trypsinized CHO cells ($2 \times 10^3$) in media (100 μL) were loaded on a 96-well plate. After incubation for 36 h, the media was replaced with fresh media (100 μL) containing increasing concentrations of Compound 1 in DMSO (final [DMSO]=1%). After 48 h of incubation, the cells in each well were washed with PBS (2×100 μL) and detached by treatment with a solution of trypsin (50 μL, 5 min). The cell suspension (10 μL) was transferred to an opaque 96-well plate containing PBS (170 μL per well) and treated with CellTiter-Glo reagent (20 μL, Promega) according to the Promega protocol provided with the reagent. After incubation at ambient temperature (22° C.) for 10 min, the luminescence of the samples was measured with a Packard Fusion microplate reader.

Inhibiting Endosome Acidification
CHO Cells

Exponentially growing CHO cells were cultivated on round collagen-coated coverslips (22 mm, BD BioCoat) in a six-well plate ($1.2 \times 10^5$ cells/well, 2 mL). After 24 h, the media was replaced with fresh media containing chloroquine (final concentration=5 μM) in DMSO (final [DMSO]=1%) and cells were incubated at 37° C. for 1 h. The media was replaced with fresh media containing Compound 3 (5 μM) and Compound 2 (concentration=8 μM) in DMSO (final [DMSO]=1%) with or without chloroquine 5% (final concentration=5 μM) in DMSO (final [DMSO]=1%). The cells were incubated at 37° C. for 24 h. The cells were washed with PBS (2×2 mL) prior to analysis by confocal microscopy.

Jurkat Cells

Jurkat lymphocytes ($5 \times 10^5$) in media (500 μL) were pre-treated with bafilomycin A1 (final concentration=1 μM) in DMSO (final [DMSO]=2%) for 1 h. To these cells was added 3 (final concentration=2.5 mM) and 2 (final concentration=2 μM) in DMSO (final [DMSO]=1%). After incubation at 37° C. for 12 h, the cells were washed with fresh media (500 μL) and resuspended in fresh media (125 μL) for analysis by confocal microscopy.

The invention claimed is:

1. A delivery system for introducing a cargo molecule into cytosol of a living cell, the system comprising:
   a first membrane binding element linked to an endosomal compartment disrupting element through a first linker having one or more anionic moieties; and
   a second membrane binding element linked to an exogenous cargo molecule through a second linker having one or more anionic moieties, the second linker having a region that is selectively cleavable, wherein the first and second membrane binding elements both induce endocytosis into an early/recycling endosome and the endosomal compartment disrupting element destabilizes the early/recycling endosome such that the exogenous cargo molecule is released from the second membrane binding element and into the cytosol of the living cell.

2. A system as in claim 1, wherein the first and second membrane binding elements are both cholesterylamine derivatives or dihydrocholesterylamine derivatives.

3. A system as in claim 2, wherein the first and second membrane binding elements are both N-alkyl-cholesteryl amine derivatives 3β-amino-5alpha-cholestane or derivatives thereof.

4. A system as in claim 3, wherein the first and second linkers are both between C1-C20 atoms or hetero-atoms.

5. A system as in claim 4, wherein the one or more anionic moieties of both the first and second linker are located in the linker proximal to the N-alkyl-cholesterylamine derivatives relative to the endosomal compartment disrupting element or cargo molecule.

6. A system as in claim 5, wherein each linker comprises two or more anionic moieties that each comprise an acidic functional group.

7. A system as in claim 6, wherein the acidic functional groups are from acidic amino acid side groups of aspartic acid and/or glutamic acid.

8. A system as in claim 6, wherein the linker region that is selectively cleavable includes a substrate for a protease.

9. A system as in claim 8, wherein the protease is present in a specific type of cell.

10. A system as in claim 9, where the specific type of cell is a cancerous cell.

11. A system as in claim 6, wherein the linker comprises a region that is selectively cleavable by a substance having a higher concentration in cytosol than in extracellular locations or a lysosome.

12. A system as in claim 11, wherein the region that is selectively cleavable is a disulfide.

13. A system as in claim 1, wherein the endosomal compartment disrupting element comprises at least one of a PC4 peptide, a PC4 peptide related sequence, a PC4 D-peptide variant that comprises at least one D-amino acid, a peptidomimetic, derivatives thereof, and combinations thereof.

14. A system as in claim 13, wherein the PC4 peptide has an amino sequence SSAWWSYWPPVA (SEQ ID NO: 1).

15. A system as in claim 1, wherein the exogenous cargo molecule is selected from the group consisting of drugs, prodrugs, molecular probes, proteins, polynucleotides, DNA, RNA, siRNA, PNA, morpholinos, carbohydrates, or lipids, and combinations thereof.

16. A system as in claim 1, wherein the cargo molecule is a cancer therapeutic agent.

17. A delivery platform for introducing a cargo molecule into cytosol of a living cell, the platform comprising:
   a membrane binding element capable of being involved in an early/recycling endosome system;
   a branched ionic linker linked to the membrane binding element, the linker having a selectively cleavable region and one or more anionic moieties;
   an endosomal compartment disrupting element linked to a branch of the branched ionic linker; and
   an exogenous cargo molecule linked to a branch of the branched ionic linker through the selectively cleavable region, wherein the membrane binding element induces endocytosis into an early/recycling endosome and the endosomal compartment disrupting element destabilizes the early/recycling endosome such that the exogenous cargo molecule is released from the early/recycle endosome and into the cytosol of the living cell.

18. A platform as in claim 17, wherein the membrane binding elements is a N-alkyl-cholesterylamine derivative or dihydrocholesterylamine derivative, the linker comprises two or more contiguous anionic moieties that comprise acidic functional groups, and the endosomal compartment disrupting element is a natural or synthetic polymer or oligomer or polypeptide.

19. A platform as in claim 18, wherein the acidic functional groups are from aspartic acid and/or glutamic acid groups.

20. A platform as in claim 18, wherein the linker region that is selectively cleavable comprises a substrate for a protease or is selectively cleavable by a substance having a higher concentration in cytosol than in extracellular locations or a lysosome.

21. A platform as in claim 18, wherein the endosomal compartment disrupting element includes at least one of a PC4 peptide, a PC4 peptide related sequence, a PC4 D-peptide variant that includes at least one D-amino acid, a peptidomimetic, derivatives thereof, and combinations thereof.

22. A platform as in claim 21, wherein the PC4 peptide has an amino sequence SSAWWSYWPPVA (SEQ ID NO: 1).

23. A platform as in claim 18, wherein the exogenous cargo molecule is selected from the group consisting of drugs, prodrugs, molecular probes, polypeptides, proteins, polynucleotides, DNA, RNA, siRNA, carbohydrates, or lipids, and combinations thereof.

24. A platform as in claim 23, wherein the siRNA is a cancer therapeutic.

25. A method for introducing a cargo molecule into cytosol of a living cell, the method comprising:
   providing the delivery system as in claim 1; and
   administering the delivery system to a subject having the living cell such that the first and second membrane binding elements associate with the living cell so as to induce endocytosis of the delivery system into an early/recycling endosome that acidifies so as to induce the endosomal compartment disrupting element to destabilize the endosome so that cytosol enters into the endosome and cleaves the selectively cleavable region so as to allow for the release of the cargo molecule from the early/recycling endosome into the cytosol.

26. A method for introducing a cargo molecule into cytosol of a living cell, the method comprising:
   providing the delivery system as in claim 1;
   administering the delivery system to a subject having the living cell such that the first and second membrane binding elements associate with the living cell so as to induce endocytosis of the delivery system into an early/recycling endosome;
   exposing the selectively cleavable region to a protease or cytosol substance that cleaves the cleavable region; and
   disrupting the endosome with the endosomal compartment disrupting element to release of the cargo molecule from the early/recycling endosome into the cytosol.

27. A method for introducing a cargo molecule into cytosol of a living cell, the method comprising:
- providing the delivery platform as in claim 17; and
- administering the delivery system to a subject having the living cell such that the membrane binding element associates with the living cell so as to induce endocytosis of the delivery system into an early/recycling endosome that acidifies so as to induce the endosomal compartment disrupting element to destabilize the endosome so that cytosol enters into the endosome and cleaves the selectively cleavable region so as to allow for the release of the cargo molecule from the early/recycling endosome into the cytosol.

28. A method for introducing a cargo molecule into cytosol of a living cell, the method comprising:
- providing the delivery platform as in claim 17;
- administering the delivery system to a subject having the living cell such that the membrane binding element associates with the living cell so as to induce endocytosis of the delivery system into an early/recycling endosome;
- exposing the selectively cleavable region to a protease or cytosol substance that cleaves the cleavable region; and
- disrupting the endosome with the endosomal compartment disrupting element to release of the cargo molecule from the early/recycling endosome into the cytosol.

29. The system of claim 1, wherein one or both the first linker and second linker includes two or more contiguous anionic moieties.

30. The system of claim 29, wherein the two or more contiguous anionic moieties are independently selected from aspartic acid or glutamic acid.

31. The system of claim 30, wherein the two or more contiguous anionic moieties of the second linker are between the second membrane binding element and the region that is selectively cleavable.

32. The system of claim 30, comprising:
- one or more hexanoic amide moieties between the two or more contiguous anionic moieties and the endosomal compartment disrupting element; and
- one or more hexanoic amide moieties between the two or more contiguous anionic moieties and the region that is selectively cleavable.

33. The system of claim 32, comprising:
- the first membrane binding element being a cholesterylalmine and having alkyl carboxyl between the cholesterylalmine and the two or more contiguous anionic moieties; and
- the second membrane binding element being a cholesterylalmine and having alkyl carboxyl between the cholesterylalmine and the two or more contiguous anionic moieties.

* * * * *

UNITED STATES PATENT AND TRADEMARK OFFICE
CERTIFICATE OF CORRECTION

PATENT NO. : 8,889,631 B2  
APPLICATION NO. : 12/543313  
DATED : November 18, 2014  
INVENTOR(S) : Peterson Page 1 of 1

It is certified that error appears in the above-identified patent and that said Letters Patent is hereby corrected as shown below:

In the specification

In Column 7, Line 38, delete "disrupter" and insert -- disruptor --, therefor.

In Column 7, Line 58, delete "disrupter" and insert -- disruptor --, therefor.

In Column 7, Lines 61-62, delete "disrupter" and insert -- disruptor --, therefor.

In Column 8, Line 4, delete "disrupter" and insert -- disruptor --, therefor.

In Column 8, Line 8, delete "disrupter" and insert -- disruptor --, therefor.

In Column 8, Line 14, delete "disrupter" and insert -- disruptor --, therefor.

In Column 14, Line 15, delete "disrupter" and insert -- disruptor --, therefor.

In Column 14, Line 65, delete "disrupter" and insert -- disruptor --, therefor.

In Column 15, Line 1, delete "disrupter" and insert -- disruptor --, therefor.

In Column 22, Line 1, delete "H tert" and insert -- tert --, therefor.

In the claims

In Column 37, Line 42, in Claim 10, delete "where" and insert -- wherein --, therefor.

In Column 37, Line 59, in Claim 15, delete "probes," and insert -- probes, polypeptides, --, therefor.

Signed and Sealed this  
Twenty-ninth Day of December, 2015

Michelle K. Lee  
*Director of the United States Patent and Trademark Office*

SEQUENCE LISTING

<160> NUMBER OF SEQ ID NOS: 9

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ser Ala Trp Trp Ser Tyr Trp Pro Pro Val Ala
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Aminohexanoic acid

<400> SEQUENCE: 2

Glu Glu Xaa Xaa Ser Ser Ala Trp Trp Ser Tyr Trp Pro Pro Val Ala
1               5                   10                  15

<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Leu Phe Glu Ala Ile Glu Gly Phe Ile Glu Asn Gly Trp Glu Gly
1               5                   10                  15

Met Ile Asp Gly Trp Tyr Gly
            20

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Leu Gly Leu Ala Ala Leu
1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Glu Glu Glu
1

```
<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Aminohexanoic acid

<400> SEQUENCE: 6

Glu Lys Xaa Xaa Ser Ser Ala Trp Trp Ser Tyr Trp Pro Pro Val Ala
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(4)
<223> OTHER INFORMATION: Aminohexanoic acid

<400> SEQUENCE: 7

Glu Xaa Xaa Xaa Ser Ser Ala Trp Trp Ser Tyr Trp Pro Pro Val Ala
1               5                   10                  15

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Aminohexanoic acid

<400> SEQUENCE: 8

Glu Glu Xaa Xaa Ser Ser Ala Trp Trp Ser Tyr Trp Pro Pro Leu Gly
1               5                   10                  15

Leu Ala Gly Glu Glu Glu Glu
            20

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 9

Xaa Gly Pro Leu Gly Leu Ala Ala Leu
1               5
```